United States Patent
Mistry et al.

(10) Patent No.: US 11,364,064 B2
(45) Date of Patent: Jun. 21, 2022

(54) SURGICAL TOOL WITH AN ASEPTIC POWER MODULE THAT ENTERS A SPECIFIC STATE BASED ON THE TYPE OF HANDPIECE TO WHICH THE POWER MODULE IS ATTACHED

(71) Applicant: Stryker Far East, Inc., Kalamazoo, MI (US)

(72) Inventors: Viren Mistry, Gurgaon (IN); Steven J. Carusillo, Kalamazoo, MI (US)

(73) Assignee: Stryker Far East, Inc., Kalamazoo, MI (US)

( * ) Notice: Subject to any disclaimer, the term of this patent is extended or adjusted under 35 U.S.C. 154(b) by 7 days.

(21) Appl. No.: 16/942,832

(22) Filed: Jul. 30, 2020

(65) Prior Publication Data
US 2020/0352619 A1    Nov. 12, 2020

Related U.S. Application Data

(60) Division of application No. 15/496,609, filed on Apr. 25, 2017, now Pat. No. 10,751,104, which is a
(Continued)

(51) Int. Cl.
*A61B 18/00* (2006.01)
*A61B 17/16* (2006.01)
(Continued)

(52) U.S. Cl.
CPC .......... *A61B 18/00* (2013.01); *A61B 17/1622* (2013.01); *A61B 17/1659* (2013.01);
(Continued)

(58) Field of Classification Search
CPC ...... A61B 18/00; A61B 17/1659; A61B 17/32
(Continued)

(56) References Cited

U.S. PATENT DOCUMENTS

| 4,768,496 A | 9/1988 | Kreizman et al. |
| 4,989,323 A | 2/1991 | Casper et al. |

(Continued)

FOREIGN PATENT DOCUMENTS

| CN | 203029323 U | 7/2013 |
| CN | 103230284 A | 8/2013 |

(Continued)

OTHER PUBLICATIONS

Depuy Synthes Power Tools, "TRS Power Module", 2013, 1 page.
(Continued)

*Primary Examiner* — David Luo
(74) *Attorney, Agent, or Firm* — Howard & Howard Attorneys PLLC

(57) ABSTRACT

A surgical handpiece includes a shell, an energy applicator, a transmission component, a lid, a latch and a data tag. The shell defines a void for receiving a power module and an opening through which the power module is inserted into and removed from the void. The energy applicator is attached to the shell. The energy applicator, when actuated, outputs energy for application to a tissue to perform a medical/surgical task. The transmission component is disposed in the shell for transmitting energy output by the power module to the energy applicator. The lid moveably is mountable to the shell to cover the shell opening. The latch is moveably attached to the shell or the lid for holding the lid in a latched state. The data tag is mounted to the latch so as to move with the latch, the data element including data identifying the handpiece.

13 Claims, 16 Drawing Sheets

Related U.S. Application Data continuation of application No. PCT/US2015/057938, filed on Oct. 29, 2015.

(51) Int. Cl.
    *A61B 90/90*     (2016.01)
    *A61B 17/32*     (2006.01)
    *A61B 17/00*     (2006.01)

(52) U.S. Cl.
    CPC .............. *A61B 17/32* (2013.01); *A61B 90/90* (2016.02); *A61B 2017/0046* (2013.01); *A61B 2017/00477* (2013.01); *A61B 2017/00734* (2013.01); *A61B 2018/00702* (2013.01); *A61B 2018/00916* (2013.01)

(58) Field of Classification Search
    USPC ..................................................... 318/3, 34
    See application file for complete search history.

(56) References Cited

U.S. PATENT DOCUMENTS

| | | | |
|---|---|---|---|
| 5,523,679 | A | 6/1996 | Kalb |
| 5,553,675 | A | 9/1996 | Pitzen et al. |
| 5,712,543 | A | 1/1998 | Sjostrom |
| 5,747,953 | A | 5/1998 | Philipp |
| 6,018,227 | A | 1/2000 | Kumar et al. |
| 6,037,724 | A * | 3/2000 | Buss ................. A61B 17/1626 439/71 |
| 6,564,242 | B1 | 5/2003 | Bonet et al. |
| 6,639,332 | B2 | 10/2003 | Metzler et al. |
| 7,178,727 | B2 * | 2/2007 | Yoked ............. G06K 19/07703 235/383 |
| 7,253,541 | B2 | 8/2007 | Kovarik et al. |
| 7,429,430 | B2 | 9/2008 | Mooty et al. |
| 7,517,351 | B2 | 4/2009 | Culp et al. |
| 7,638,958 | B2 * | 12/2009 | Philipp ............ A61B 17/32002 318/139 |
| 7,998,157 | B2 | 8/2011 | Culp et al. |
| 8,241,235 | B2 | 8/2012 | Kahler et al. |
| 8,439,939 | B2 | 5/2013 | Deville et al. |
| 8,440,028 | B2 | 5/2013 | Christmann et al. |
| 8,564,242 | B2 | 10/2013 | Hansford et al. |
| 9,023,014 | B2 | 5/2015 | Chowaniec et al. |
| 9,198,642 | B2 | 12/2015 | Storz |
| 9,241,757 | B2 | 1/2016 | Beardsley et al. |
| 9,456,873 | B2 | 10/2016 | Beardsley et al. |
| 2006/0206100 | A1 | 9/2006 | Eskridge et al. |
| 2006/0217729 | A1 | 9/2006 | Eskridge et al. |
| 2008/0077149 | A1 | 3/2008 | Hoegerle |
| 2011/0011434 | A1 | 1/2011 | Hagelstein et al. |
| 2013/0020102 | A1 | 1/2013 | Bjornlinger et al. |
| 2013/0240230 | A1 | 9/2013 | Saur |
| 2013/0240231 | A1 | 9/2013 | Storz et al. |
| 2013/0340553 | A1 | 12/2013 | Durrenberger et al. |
| 2014/0008090 | A1 | 1/2014 | Kokinelis et al. |
| 2014/0100687 | A1 | 4/2014 | Ekstrom et al. |
| 2014/0113243 | A1 | 4/2014 | Boutoussov et al. |
| 2014/0232316 | A1 | 8/2014 | Philipp |
| 2017/0224400 | A1 | 8/2017 | Mistry et al. |

FOREIGN PATENT DOCUMENTS

| | | |
|---|---|---|
| CN | 103230285 A | 8/2013 |
| CN | 103637825 A | 3/2014 |
| CN | 205758727 U | 12/2016 |
| DE | 10124537 A1 | 2/2002 |
| DE | 102012015093 A1 | 2/2014 |
| EP | 1214913 A2 | 6/2002 |
| EP | 2716408 A2 | 4/2014 |
| WO | 2008021687 A1 | 2/2008 |
| WO | 2008126685 A2 | 10/2008 |
| WO | 2008134358 A1 | 11/2008 |
| WO | 2012061739 A1 | 5/2012 |
| WO | 2012088141 A2 | 6/2012 |
| WO | 2012118416 A1 | 9/2012 |
| WO | 2012134471 A1 | 10/2012 |
| WO | 2013177423 A2 | 11/2013 |
| WO | 2014193826 A1 | 12/2014 |

OTHER PUBLICATIONS

English language abstract and machine-assisted English translation for CN 203029323 extracted from espacenet.com database on Dec. 7, 2017, 7 pages.

English language abstract for CN 103230284 extracted from espacenet.com database on Dec. 7, 2017, 2 pages.

English language abstract for CN 103230285 extracted from espacenet.com database on Dec. 7, 2017, 2 pages.

English language abstract for CN 103637825 extracted from espacenet.com database on May 20, 2019, 2 pages.

English language abstract for CN 205758727 extracted from espacenet.com database on May 20, 2019, 2 pages.

English language abstract for DE 101 24 537 extracted from espacenet.com database on Dec. 7, 2017, 2 pages.

EPO "ISA Search Report and Written Opinion for PCT App. No. PCT/US2015/057938".

Nouvag, "HighTorQ Power Tools for Major Bone Surgery", 2014, 24 pages.

Synthes, Inc. Power Tools, "Trauma Recon System (TRS) User Manual", 2009, pp. 1-52.

* cited by examiner

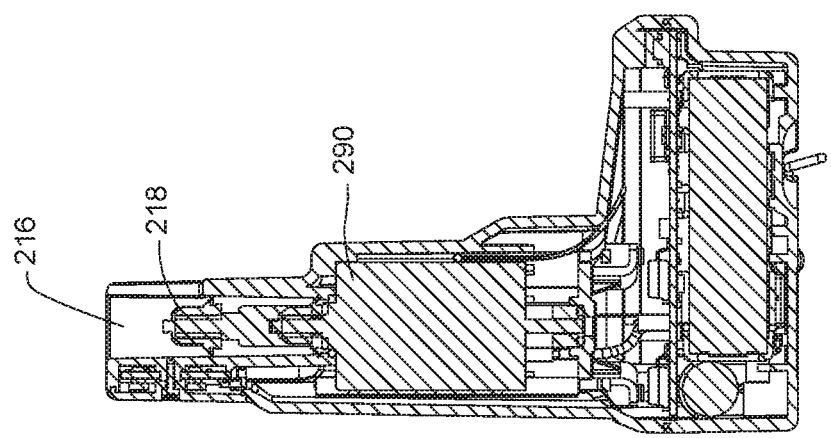
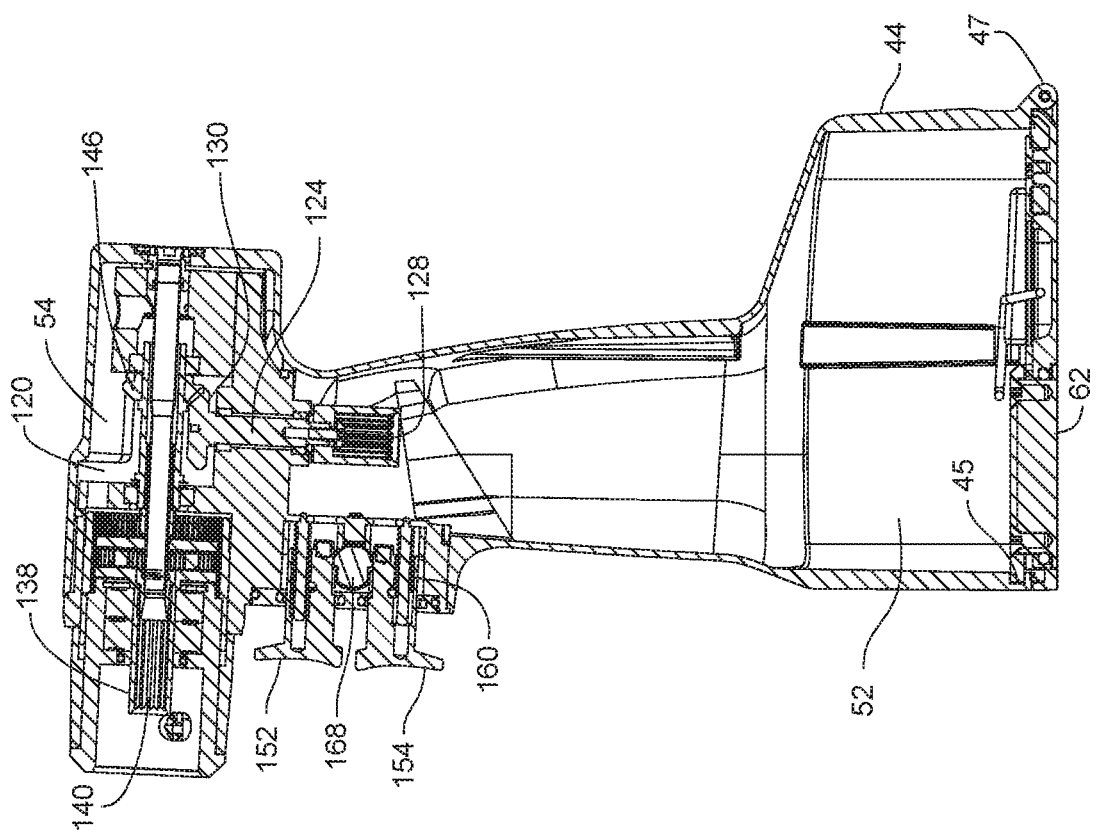

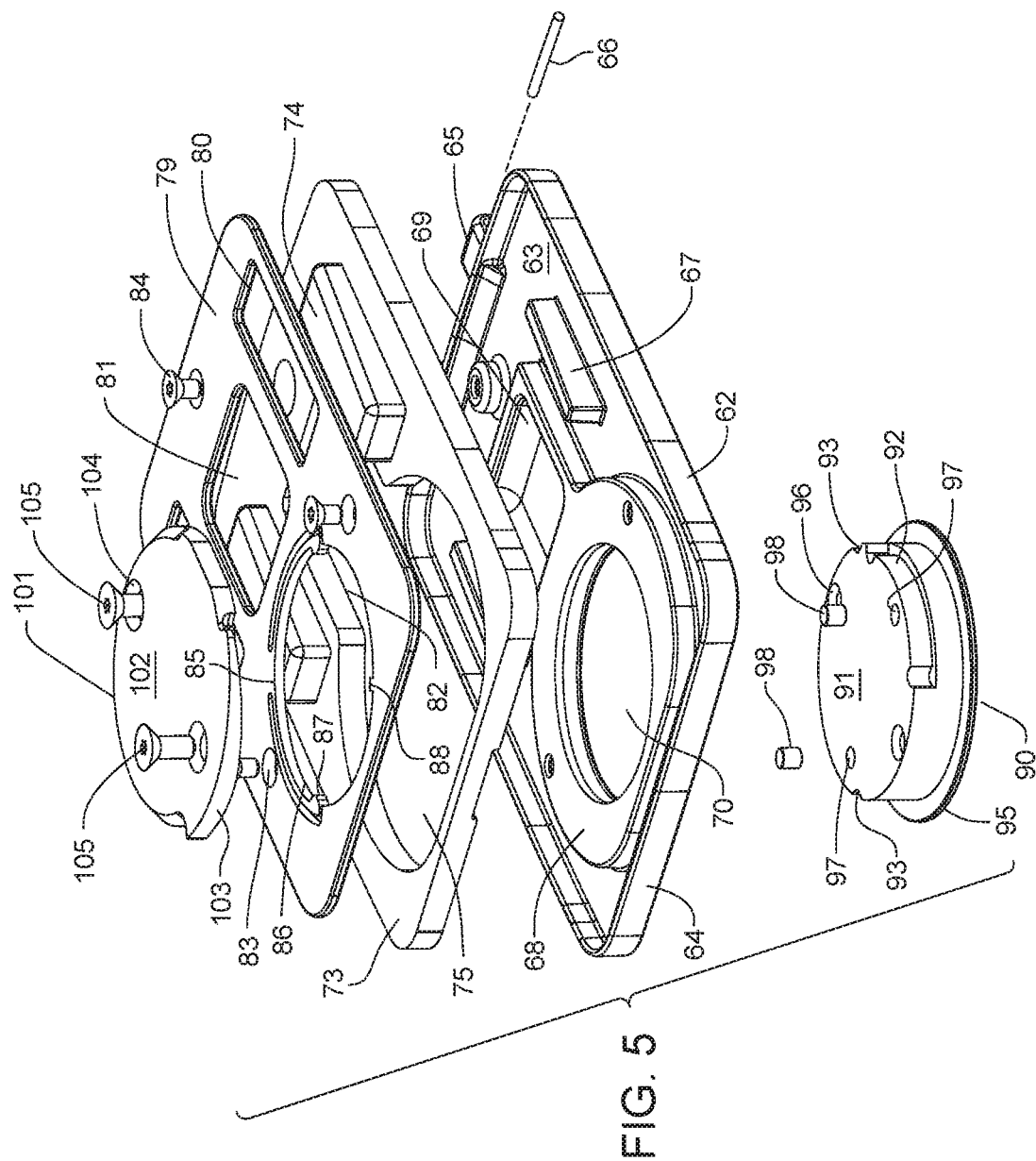

SURGICAL TOOL WITH AN ASEPTIC POWER MODULE THAT ENTERS A SPECIFIC STATE BASED ON THE TYPE OF HANDPIECE TO WHICH THE POWER MODULE IS ATTACHED

FIELD OF THE INVENTION

This invention is generally directed to a powered surgical tool that includes a sterilizable handpiece and an unsterilzable, aseptic, power module. The tool of this invention is configured so that the power module detects the type of handpiece to which the module is attached and sources power as a function of the type of handpiece.

BACKGROUND OF THE INVENTION

In modern surgery, one of the most important instruments available to medical personnel is the powered surgical tool. One form of a powered surgical tool is a handpiece in which a motor is housed. Secured to the handpiece is a cutting attachment designed for application to a surgical site to perform a specific medical procedure. Some powered surgical tools are provided with drills, burs or reamers for cutting bores into tissue or for selectively removing tissue such as bone. Other motorized powered surgical tools are provided with saw heads. These tools separate large sections of hard and soft tissue. A wire driver is a power tool that, as its name implies, drives a wire into a patient, more particularly, a bone. Power tools are also used to perform other functions in the operating room. For example, it is known to use a power tool to mix the components that form a mass of surgical cement. Other powered surgical tools include power generating units such as ultrasonic drivers or devices that emit photonic (light) energy.

The ability to use powered surgical tools on a patient lessens the physical strain of surgeons when performing medical procedures on a patient. Moreover, most surgical procedures can be performed more quickly and more accurately with powered surgical tools than with the manual equivalents that preceded them.

One type of powered surgical tool that is especially popular with some physicians is the cordless, battery-operated powered surgical tool. As the name implies, this tool has a battery that functions as the power source for the tool power generating unit. This eliminates the need to provide the tool with a power cord connected to an external-power source. Elimination of the power cord offers benefits over corded, powered surgical tools. Surgical personnel using this type of tool do not have to concern themselves with sterilizing a cord so the cord can be introduced into the sterile surgical field or ensuring that, during a procedure, an unsterilized section cord is not inadvertently introduced into the surgical field. Elimination of the cord also results in the like elimination of the physical clutter and field-of-view blockage a cord brings to a surgical procedure.

There are differences between conventional power tools and power tools designed to perform surgical procedures. A power tool designed to perform a surgical procedure must be able to withstand the rigors autoclave sterilization. In an autoclave sterilization process, the tool is placed in a chamber in which the atmosphere is saturated with water vapor (steam) the temperature can exceed 110° C. and the pressure exceeding 290 torr. Internal components of the tool, including the electrical components of any circuit, if left unprotected in and repeatedly exposed to this environment, corrode.

One solution to prevent this type of corrosion is to housing as many electrical conductive components of the tool in sealed modules or sealed shells. The Applicant's U.S. Pat. No. 7,638,958/PCT Pub. No. WO 2007/002180A2, the contents of which are explicitly incorporated herein by reference by reference, discloses how many of the components associated with a motorized powered surgical tool can be incorporated into a single sealed module.

The assembly of the above publications does a more than adequate job of protecting many of the electrical components of a powered surgical tool from the adverse effects of sterilization. However, over time the joints of the sealed module can breakdown. Also, the motor, the rotor and windings, of this tool is not protected to the extent the components in the sealed module are protected. Further, it can be expensive to provide a tool with the protection provided by this sealed module.

Another solution to this problem is to divide the components of the tool into two parts, one that is sterilized and one that is not sterilized. More specifically, this type of tool includes a power module and a handpiece. The power module includes the power generating unit, for example a motor. Also disposed inside the power module are cells that store charge used to activate the power generating unit. The power generating unit includes a control circuit. The control circuit regulates the activation of the power generating unit. The body, the shell, of this power generating unit, as well as the components internal to the body, are not designed to withstand the sterilization process.

The second part of the tool is the handpiece. The handpiece includes a body or shell. Internal to the handpiece body is a void for receiving the power generating unit. A handpiece also includes some sort of transmission. The transmission is capable of transmitting the power output by the power generating unit to the attached implement that is applied to the patient to perform the desired procedure. Often the handpiece includes some sort of coupling components. The coupling components facilitate the releasable attachment of the implement to the transmission. The handpiece body and the attached components are designed to withstand the rigors of the sterilization process.

When a tool with an aseptic power module is prepared for use, the handpiece is sterilized. The power module is placed in the closed void internal to the handpiece. This seals the unsterilized power module from the environment around the patient. The tool is then used in the same manner in which a sterilizable tool is used. The power generating unit is actuated to cause the implement to perform the desired procedure on the patient.

A benefit of the above described type of tool is that only the handpiece and its internal components need to be designed to withstand sterilization. This makes it less expensive to provide this type of tool in comparison to a tool the whole of which is subjected to sterilization. Further, since the aseptic power module of this tool is not subjected to sterilization, there is no possibility that this module will, as a result of being exposed to the sterilization process, malfunction.

While the above type of tool is useful, there are limitations associated with the tool. Some of these limitations are due to the tact that many power surgical tools, while similar in shape, are different in operation. For example, two motorized powered surgical tools a surgeon may employ are a wire driver and a sagittal saw. Both tools include a motor. The tools are designed to drive different implements. The wire driver is designed to rotate a wire or a pin. A sagittal saw is designed oscillate a blade back and forth in plane around an axis that extends through the plane in which the blade moves. Difficulties can arise if one inadvertently place a power module designed for use with the handpiece of one of these tools into the handpiece of the other tool.

One suggested solution to this problem is to provide a switch on the power module. At one point during the process of assembling the tool for use is that the switch is manually set to indicate the type of handpiece to which the power module is coupled. A disadvantage of this solution is that it requires the individuals preparing the tool for use to properly set the switch.

SUMMARY OF THE INVENTION

The invention is related to a new and useful surgical power tool. The power tool of this invention includes both a sterilizable handpiece and an aseptic power module. The tool of this invention is designed so that the power module automatically sources power to different handpieces as a function of the power requirements specific to each handpiece.

The handpiece of the tool of this invention includes a data tag. The data tag stores data identifying which the specific type of handpiece from plural different types of handpieces. The power module includes a reader and a controller. The reader reads the data from the handpiece data tag. The controller receives the signal from the reader that identifies the type of handpiece. Based on the type of handpiece, the controller the power generating unit internal to the power module to source power appropriate to the type of handpiece to which the module is attached.

In some preferred versions of the invention the handpiece data tag is integral with the latch used to hold the power module to the handpiece. The absence/presence of the data signal from the data tag is further employed by control circuit as an indicia that the power module is properly coupled to the handpiece and the tool is ready for use. Only after the control circuit makes determinates the lid is in a latched state does the control circuit actuate the tool power generating unit.

In some preferred version of the invention, the handpiece data tag consists of a set of one or more specifically placed magnets. The power module data reader consists of one or more sensors. Each sensor selectively outputs a signal as a function of the presence/absence of a magnet. In some versions of the invention, the sensor outputs a signal as a function of the strength of the sensed magnetic field.

In some versions of the invention, the power module power generating unit is a motor. In these versions of the invention, the handpiece transmission is a gear train that transfers the mechanical energy of the motor to the attached energy applicator or implement.

BRIEF DESCRIPTION OF THE DRAWINGS

The invention is pointed out with particularity in the claims. The above and further features and benefits of the invention are understood from the following Detailed Description taken in conjunction with the accompanying drawings in which:

FIG. 4 is a cross sectional view of the handpiece;

FIG. 5 is an exploded view of the handpiece lid;

FIG. 14 is a cross sectional view of the power module;

DETAILED DESCRIPTION

I. Overview

Figure 1:
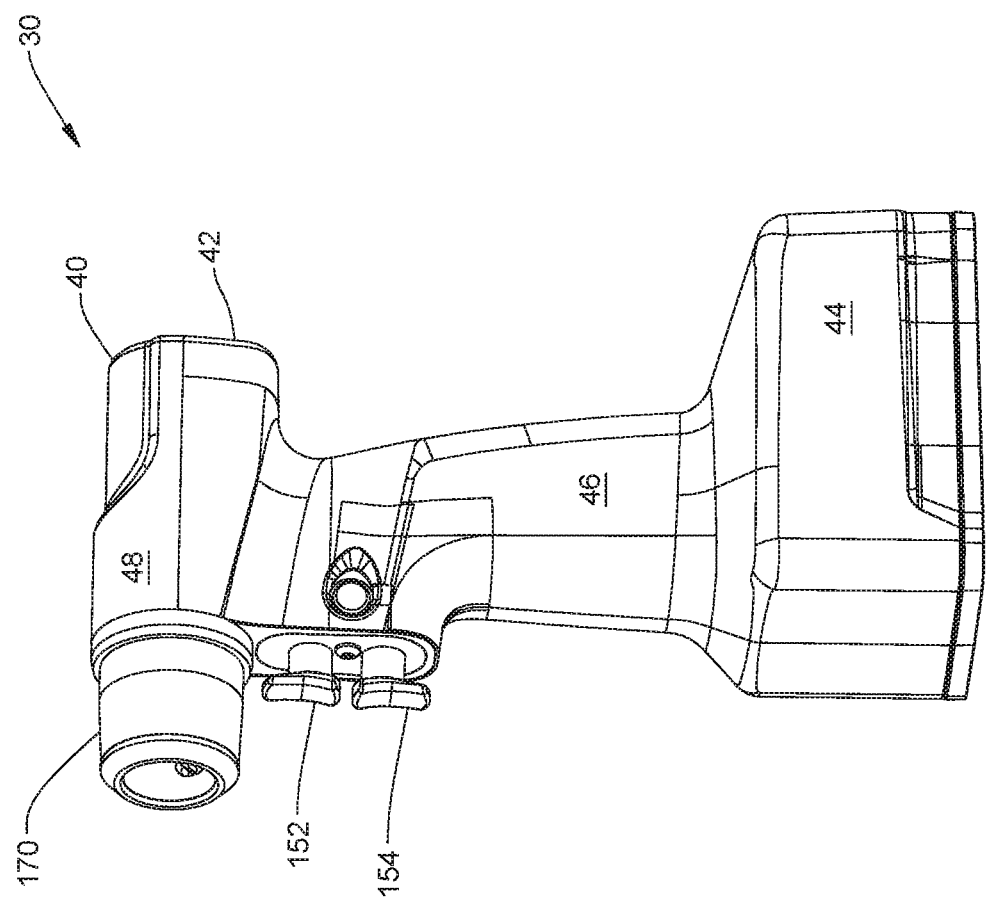
FIG. 1 is a perspective view of a surgical tool of this invention.

A powered surgical tool 30 of this invention is now generally described by reference to FIGS. 1-3. Tool 30 includes a handpiece 40 in which power module 180 is removably seated. Internal to the power module 180 is a power generating unit. In the described version of the invention, the power generating unit is a motor 290. Also disposed in the power module 180 are cells 270 and a controller 320. Cells 270 provide the charge for energizing the motor 290. Controller 320 selectively applies current to the motor 290 to regulate the actuation of the motor.

Handpiece 40 includes components to which the power output by the handpiece motor 290 is applied. One of these components is a drive spindle 136. Since the described surgical tool 30 is motorized surgical tool, the tool includes a coupling assembly 170 generally represented by a ring. Coupling assembly 170 releasably holds an energy applicator or a front end attachment to the handpiece 40. An energy applicator, for the purposes of this invention, is a device that is applied to the patient to accomplish a surgical task. Energy applicators attached to motorized surgical handpieces include drill bits, saw blades, reamers and burs. An energy applicator for this invention is also understood to be medical device that is driven into a patient for either permanent or temporary implantation. These types of devices include wires, pins and screws. In some versions of the invention, the coupling assembly is configured to removably receive a front end attachment. The front end attachment is the actual device that engages and drives the energy applicator. This allows a single tool to be used to drive different types of energy applicators.

Handpiece 40 also includes at least one control component. In the depicted version of the invention, there are two control components, triggers 152 and 154.

When use of the tool 30 is desired, one or both triggers 152 and 154 is/are selectively depressed. Sensors 302 and 304 (FIG. 13) internal to the power module 180 monitor whether or not triggers 152 and 154 are depressed. When a trigger 152 or 154 is depressed, the associated sensor 302 or 304, respectively, outputs a signal representative of the trigger state to the controller 320. In response to receipt of this signal, the controller 320 regulates the application of current to the motor to cause the desired actuation of the motor 270. More particularly, current is applied to the motor to cause the actuation of the motor that results in the actuation of the energy applicator desired by the surgeon.

II. Handpiece

Initially, it should be understood, that the components forming the handpiece 40 are able to withstand the rigors of autoclave sterilization or other sterilization process to which the handpiece may be exposed. For a component to withstand the rigors of autoclave sterilization the component should be able to withstand exposure to an environment wherein the temperature is in excess of 105° C., supersaturated steam (water vapor) at a pressure of 2 Bars is present.

Handpiece 40, as now described by FIGS. 1-4, as includes a shell 42. Shell 42 is the body or housing of the handpiece 40. The depicted shell 42 is shaped to have a base 44. In a plane perpendicular to the plane of FIG. 3, base 44 is generally rectangular in shape. The bottom end of base 44 is open. Base 44 is formed so as to have two hinge knuckles 47 (one identified) that extend proximally and slightly downwardly from the proximal end of the base. While not seen, handpiece 40 is formed so that the bottom end of the base 44 is has a rim that defines the outer perimeter of the opening into the base 44. This rim is stepped inwardly from the outer surface of the base 44. Base 44 is formed to have a slot 45, identified in FIG. 4. Slot 45 extends inwardly from the inner surface of the distally directed panel of the base 44. The shell is formed so that slot 45 is located a relatively short distance, less than 0.5 cm, above the open end of the base 44. Slot 45 does not extend through the whole of the and in which the slot is formed.

A handgrip 46, also part of shell 42, extends upwardly from base 44. In the depicted version of the invention, handgrip 46 does not rise from the center of the base 44. Instead the handgrip 46 rises from a top of the base along a top-to-bottom longitudinal axis that is distally forward of the center of the top of the base 44. (Here "distal" is understood to mean away from the person holding tool 30, towards the site to which the attached energy applicator is applied. "Proximal" is understood to mean towards the person holding the tool 30, away from the site to which the attached energy applicator is applied.). A barrel 48, also part of the shell 42, is located above handgrip 46. Barrel 48 has a proximal-to-distal longitudinal axis that is generally perpendicular to the top-to-bottom perpendicular longitudinal axis through handgrip 46. Shell 42 is formed so that barrel extends both proximally rearward from and distally forward from the handgrip 46.

The particular handpiece 40 illustrated is a device known as a dual trigger rotary handpiece. A coupling assembly 170 is mounted to the front end of barrel 48. This type of handpiece, is designed to releasably hold another surgical tool called a front end attachment (not illustrated). Coupling assembly 170 has an open front end, not identified, that is dimensioned to receive the front end attachment. The front end attachment is removably held to the handpiece shell 42 by coupling assembly 170. Internal to the front end attachment is a drive shaft. The front end attachment drive shaft is dimensioned to releasably engage and be driven by the handpiece drive spindle 136. One type of front end attachment is a chuck. The chuck is configured to releasably hold and transfer rotationally power to a rotating energy applicator such as a drill bit. Another type of front end attachment is a wire driver. A wire driver holds an energy applicator constructed to be driven into the patient for either permanent or temporary implementation. Wires and pins are two species of this type of energy applicator. The structure of these front end attachments and energy applicators is outside the scope of the present invention.

The open end of base 44 leads to a void, compartment 52, in the shell 42. The shell 42 is formed so that compartment 52 extends through the base 44 and handgrip 46. Compartment 52 opens up into a void 54 that extends through the shell barrel 48. Void 54 extends between the proximal and distal end of the barrel 48. The top of the shell 42 is formed with a keyhole shaped opening 56 (FIG. 2). The wide circular portion of opening 56 opens into the distal end of the barrel void 54. Coupling assembly 170 seats in the circular portion of opening 56. The oval portion of opening 56, the narrow width portion, opens into the portion of compartment 52 immediately below void 54. Shell 42 also is formed with two coaxial circular holes 58. Holes 58 extend through the opposed sides of the shell 42. Holes 58 open into the portion of compartment 52 below void 54.

A lid 62, now described by reference to FIGS. 4 and 5, is pivotally attached to shell base 44 adjacent the bottom opening into compartment 52. Lid 62 includes a generally planar plate 63. A rim 64 extends upwardly from and around the outer perimeter of plate 63. Collectively, the components of tool 30 are dimensioned so that the lid 62 can seat over the open end of shell base 44, and when the is so seated, the lid rim 64 seats in the stepped space located immediately outwardly from handpiece shell rim. Plural knuckles 65, one seen in FIG. 5, extend proximally rearward from the proximally directed face of lid rim 64. When handpiece 40 is assembled, the lid knuckles 65 are aligned with the handpiece shell knuckles 47. Lid 62 is pivotally connected to the shell base 44 by a pin 66 that extends through coaxial bores in the shell and lid knuckles 47 and 65, respectively.

Two parallel ribs 67, one identified, extend upwardly from the inner surface of lid plate 63. A raised island 68 also extends upwardly from the inner surface of lid 62. Island 68 has rectangular section and a circular section, (individual island sections not identified). The island rectangular section is located between and is spaced inwardly from ribs 67. The island circular section has is located distally forward from the island rectangular section. The island circular section has a diameter that is greater than the side-to-side width across the rectangular section. Lid 62 is further formed to so that the rectangular section of island 68 is formed with a recess 69. Further, an opening 70 extends through the circular section of the island 68.

A gasket 73 formed of compressible material such as silicone is seated on the inner surface of lid plate 63. Gasket has two ribs 74. The components of the handpiece 40 are formed so that when the gasket 73 is disposed over the lid plate 63, the gasket ribs 74 are located above the lid ribs 67. While not seen, the outwardly directed face of the gasket is formed with openings. These openings project into gasket ribs 74 and are dimensioned to receive the lid ribs 67. Thus, as part of the process of assembling handpiece 40, gasket 73 is seated on lid plate 63 so that the lid ribs 67 seat in the gasket ribs 74. The seating of these ribs together facilitates proper seating of gasket 73 on lid 62. The gasket 73 is further formed to have a center opening 75. Gasket center opening is dimensioned to receive lid island 68.

A plate 79, formed from stainless steel, is disposed over the surface of gasket 73 opposite the lid 62. Plate 79, like gasket 73, has a shape that is similar to the shape of lid plate 63. A difference between gasket 73 and plate 79 is that plate 79 is shorter in both length and width than gasket 73. Plate 79 is formed with a number of openings. Two of the openings, openings 80, (one opening 80 identified) are each dimensioned to receive a separate one of the gasket ribs 74. More specifically, it should be understood that the gasket ribs project up approximately 3 mm from the upwardly directed face of plate 79. Plate 79 is formed with an opening 81 that is generally in the shape of a rectangle with rounded corners. When handpiece 40 is assembled, plate opening 81 is in registration over recess 69 formed in lid 62.

A fourth opening in plate 79 is opening 82. Opening 82 is generally circular in shape. When the handpiece is assembled, opening 82 is in registration with opening 70 formed in lid 62. Plate 79 is formed with plural additional openings 83, only one identified. Openings 83 receive the fasteners 84 that hold plate 79 to lid 62. Fasteners 84 extend into threaded closed end bores 85 formed in the lid 62.

Plate 79 is further formed have two arcuately shaped beams 86. Beams 86 extend from a tab 85 that projects into opening 82. The beams 86 extend from opposed sides of tab 85. A toe 87 extends outwardly from the end of each beam 86. Toes 87 are generally directed towards the center of opening 82. Owing to the material from which plate 79 is formed, beams 86 are able to flex relative to tab 85. Plate 79 is further formed to have a tab 88 that extends into opening 82. The plate 79 is formed so that tab 88 is located between toes 87. Tab 88 extends into open A latch knob 90 and latch plate 101 are rotatably mounted to the handpiece lid 62. The latch knob 90 is shaped to define a core 91 that is generally cylindrical in shape. The outer diameter of core 91 is such that the core can rotate in lid opening 70, gasket opening 75 and plate opening 82. While core 91 is generally cylindrical, the core is formed with a step 92 that extends radially inwardly from the outer perimeter of the core. Step 92 faces the portion of the core that is directed upwardly, towards the handpiece barrel 48. Detents seen at the ends of the core are for manufacturing purposes only (detents not identified). The core 91 is further formed so that arcuately spaced from step 92 are two detents 93. Detents 93 extend inwardly from the outer cylindrical surface of the core. Each detent 93 can receive a separate one of the toes 87 integral with beams 87. When handpiece 40 is assembled, plate beams 86 seat against the curved outer surface of the core 91. Plate tab 91 seats in the space immediately above core step 92.

Latch knob 90 also has a lip 95. Lip 95 extends radially outwardly and circumfentially around the outer perimeter of knob core 91. The lip 95 extends around the outermost portion of the core 91. Upon assembly or handpiece 40, lip 95 seats in a step (not illustrated that extends inwardly from the outer surface of lid 62. This step extends circumferentially around lid opening 70.

Four closed end bores extend inwardly from the inner face of core 91. Two bores, bores 96, are formed with threading (not illustrated). Two bores, bores 97 are smooth walled.

A magnet 98 is seated in one or both of the bores 97. In the illustrated version of the invention, a magnet 98 is seated in both bores 97.

The latch plate 101 is secured over the inner face of core 91. The latch plate 101 is formed of magnetically permeable material such as 300 stainless steel. Latch plate 101 has a generally disc shaped main body 102. An arcuately shaped lip 103 extends radially outwardly from one section of the plate body 102. Lip 103 projects radially beyond the main body 102 so as to extend outwardly beyond core 91 of latch knob 90. In the illustrated version of the invention, the surface of lip 103 directed to the lid 62 is tapered. Extending arcuately from one end of the lip 103 to the opposed end, the thickness of the lip increases. Two holes 104 (one identified) extend through plate body 102.

Two fasteners 105 secure the latch plate 101 to the inner face of lid core 91. Each fastener 104 extends through one of the holes 104 into one of the threaded bores 96 formed in knob 90d. As a consequence of the latch plate 101 being secured to the exposed inner face of knob core 91, the latch plate 101 holds magnets 98 in bores 97 internal to the knob 90.

Returning to FIGS. 2-4, it can be seen that the handpiece drive spindle 136 is part of a transmission 120. Transmission 120 includes a case 122. Case 122 is designed to fit in shell void 54. A portion of case 122 also seats in the oval portion of shell opening 56 that opens into compartment 52. Two spindles, an input spindle 124 and the drive spindle 136, are parts of transmission 120 that are rotatably mounted to case 122. Input spindle 124 has a base 126 that is located below the case 122. The input spindle 124 thus projects into compartment 52. Base 126 is formed with a closed end bore 128 that extends upwardly from the bottom of the base. Not identified are the teeth that extend inwardly from the inner surface of base 126 that define bore 128. Not illustrated are the bearing assemblies that rotatably hold the input spindle 124 to case 122. The head of the input spindle 124 is a bevel shaped gear 130.

Drive spindle 136 is mounted to case 122 so that when handpiece 40 is assembled, drive spindle is centered on a longitudinal axis that is parallel to, if not collinear with the longitudinal axis through the shell void 54. Not identified are the bearing assemblies that rotatably hold the drive spindle 136 to the case 122.

The drive spindle 136 is formed to have features that facilitate the releasable coupling of the front end attachment to the spindle. In the illustrated version of the invention, these features include a head 138 that extends forward of case 122. Head 138 is formed to have a bore 140 that extends proximally rearward from the distal end of the head 138. Teeth (not identified) extend inwardly from the inner surface of the head that defines bore 140. The head is thus designed to receive toothed shaft integral with the energy applicator or front end attachment. The engagement of the shaft causes the implement or attachment shaft to rotate with the drive spindle 136.

A planetary gear assembly 142, also part of transmission 120, connects the input spindle 124 to the drive spindle 136. The planetary gear assembly includes an input shaft 144. A bevel gear 146 is located at the proximal end of shaft 144 with a bevel gear 142. Gear 146 engages input spindle gear 130. The engagement of gears 130 and 146 causes the drive spindle 136 to rotate upon the rotation of the input spindle 124. Planetary gear assembly 142 reduces the rotational speed of the drive spindle 136 relative to the input spindle 124 so as to increase the torque the drive spindle can output.

Also mounted to shell 40 are triggers 152 and 154. Triggers 152 and 154 are moveably attached to a frame 150. Frame 150 is seats in an oval portion of case 122. This oval portion of case 122 seats in the portion of compartment 52 immediately proximal to the oval portion of opening 56.

Figure 2:
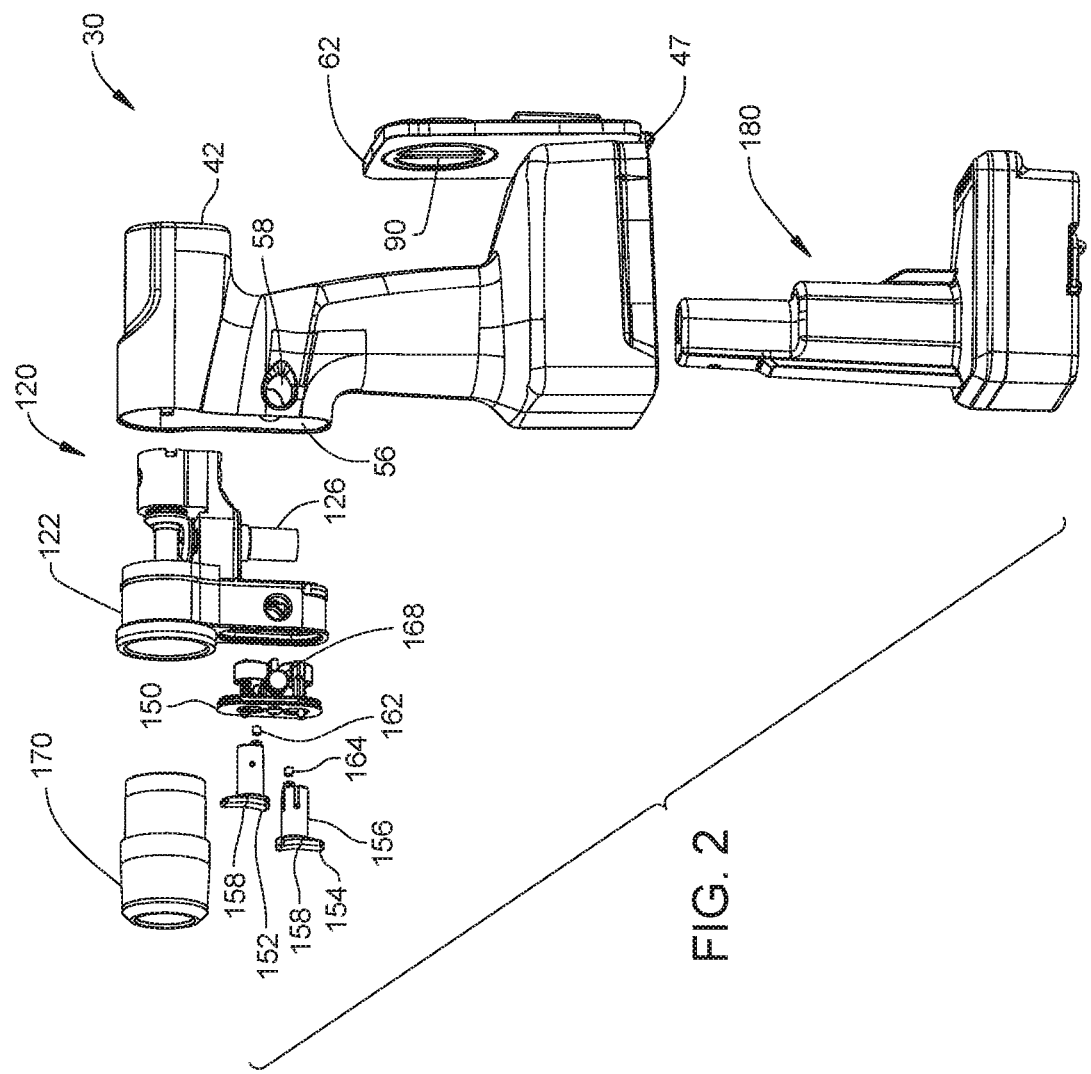
FIG. 2 is an exploded view of the components of this invention including a depiction of how a power module is fitted to a handpiece.
Figure 3:
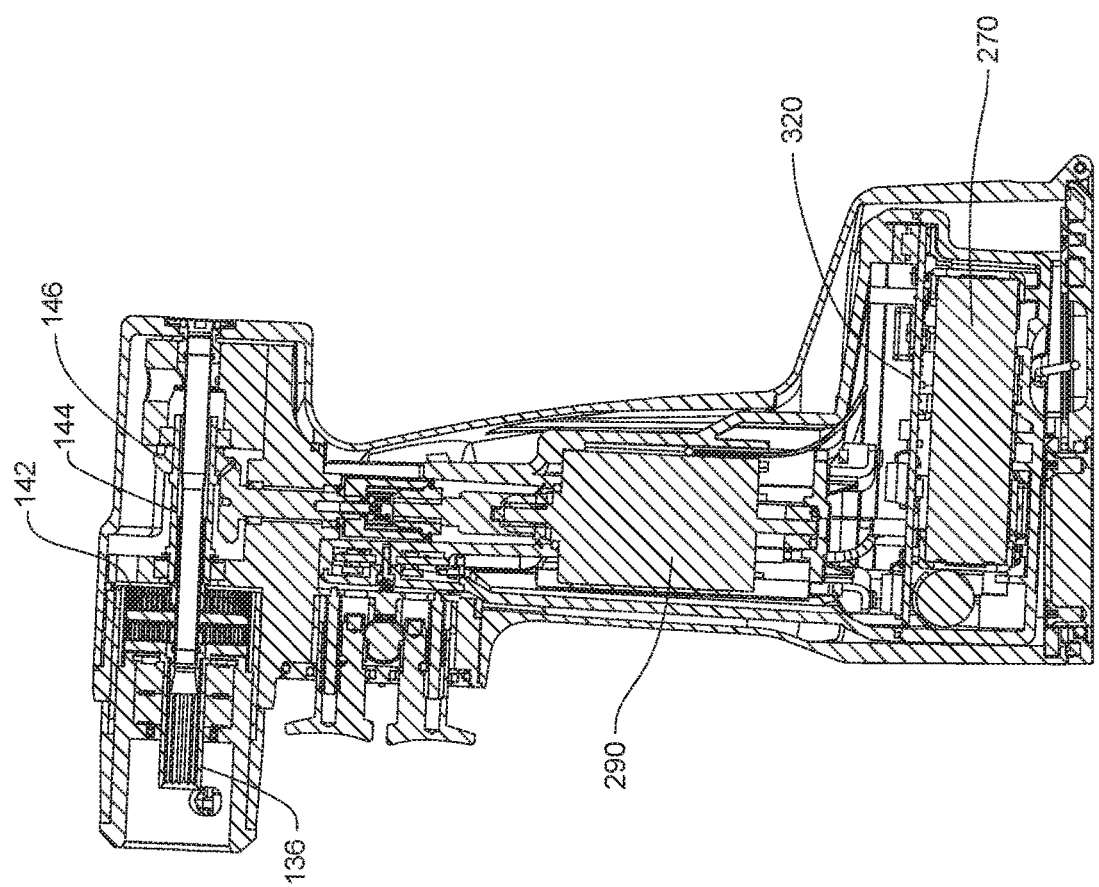
FIG. 3 is a cross sectional view of the tool of the invention.
Figure 6:
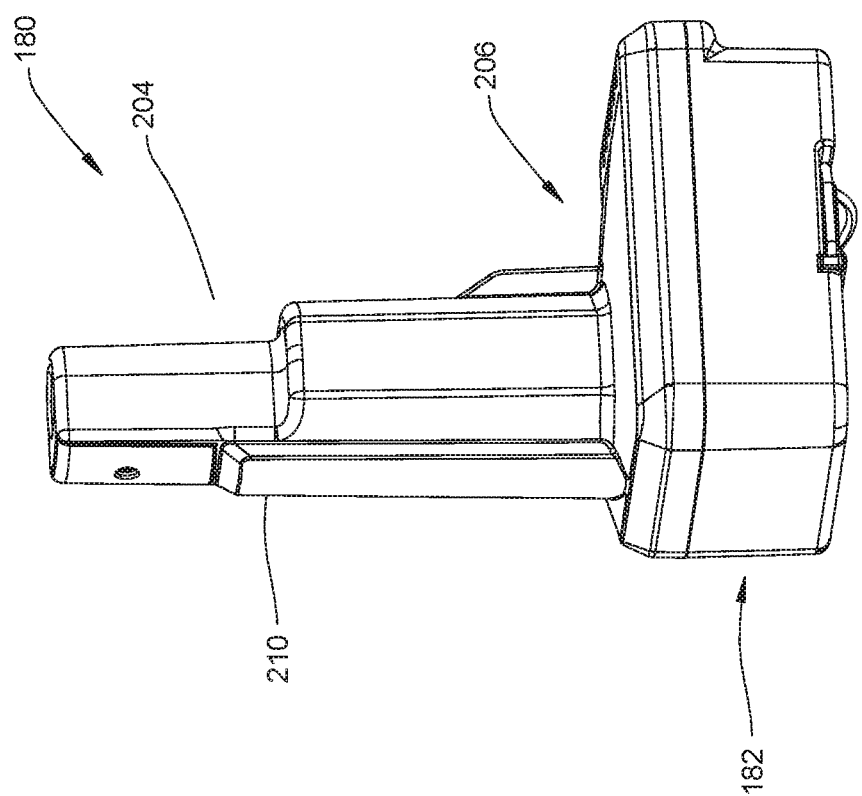
FIG. 6 is a perspective view of the power module.
Figure 8:
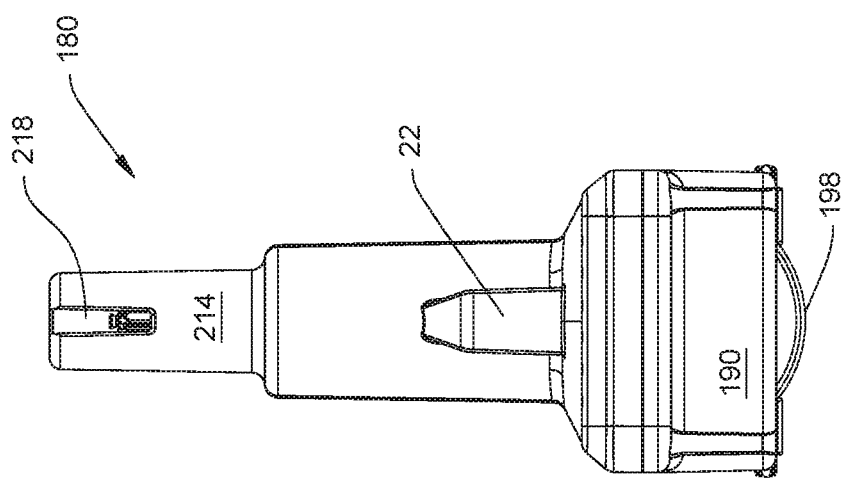
FIG. 8 is a rear plan view of the power module.
Figure 7:
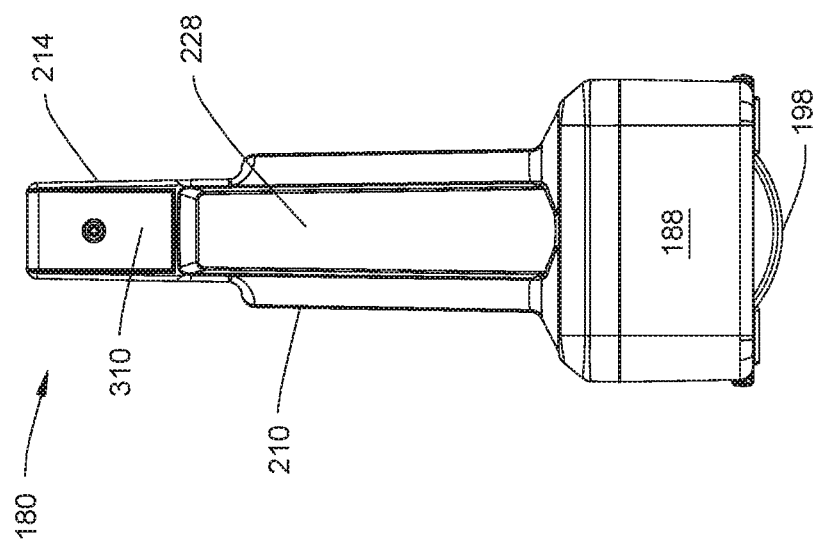
FIG. 7 is a front plan view of the power module.
Figure 10:
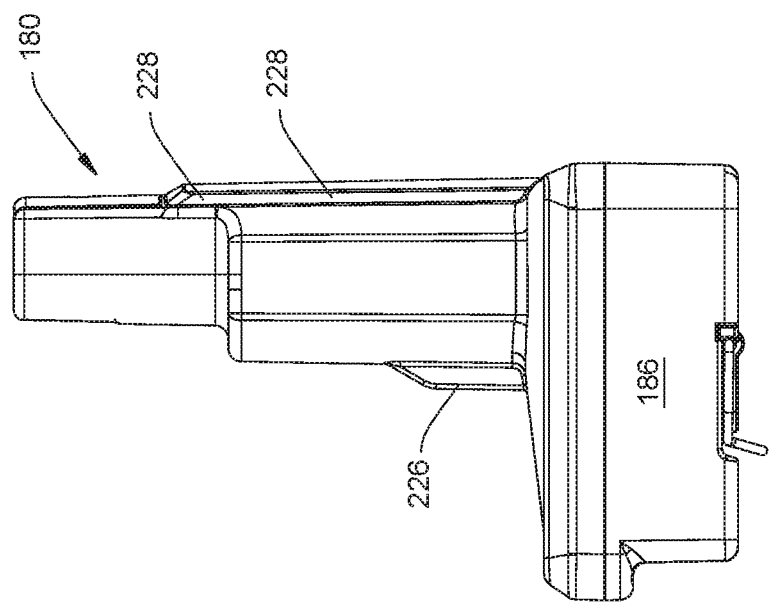
FIG. 10 is a right side plan view of the power module.
Figure 9:
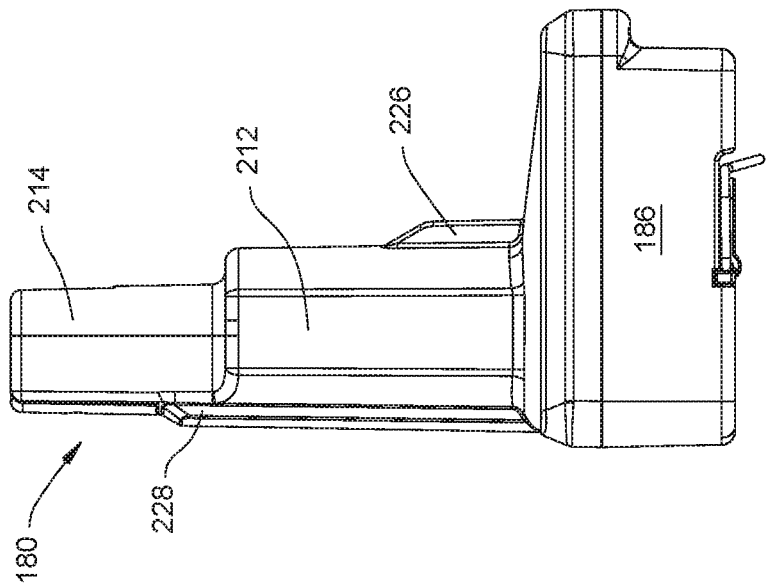
FIG. 9 is a left side plan view of the power module.
Figure 12:
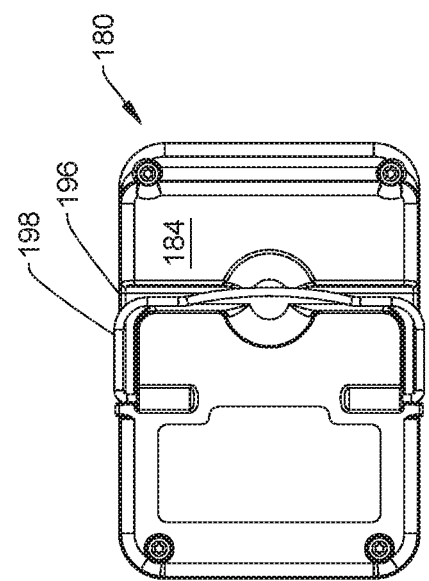
FIG. 12 is a bottom plan view of the power module.
Figure 11:
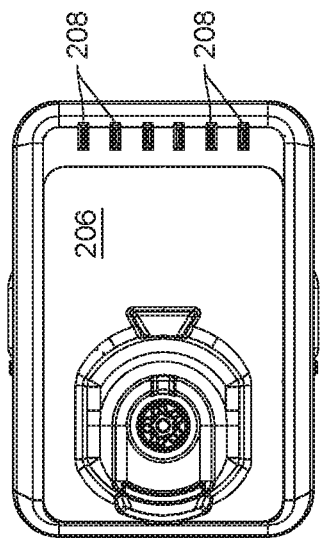
FIG. 11 is a top plan view of the power module.

Each trigger 152 and 154 includes a generally cylindrical barrel 156 (one barrel identified in FIG. 2). Barrel 156 is the portion of each trigger 152 and 154 slidably mounted to frame 150. A head 158, shaped as a finger grip, is disposed over the distal free end of the barrel. A magnet is mounted to the proximal end of the barrel. For the purposes of understanding this invention, magnet 162 is the magnet integral with trigger 152. Magnet 164 is the magnet integral with trigger 154. A spring 160 disposed between an interior surface of frame 150 and each barrel 156 exerts a force on the barrel to urge the barrel distally forward. The force exerted by spring 160 can be overcome by finger force.

Handpiece 40 also includes a rod shaped mechanical slide 168. Slide 168 is mounted to frame 150 and has ends that extend out of shell openings 58. Slide 168 is selectively positioned to prevent the unintended depression of triggers 152 and 154. The means by which slide 168 operates and the assembly employed to hold triggers 152 and 154 to frame 150 are not part of the present invention. An understanding of some of these assemblies are disclosed in U.S. Pat. No. 7,638,958/PCT Pub. No. WO 2007/002180, the contents of which is explicitly incorporated herein by reference.

III. Power Module

The power module 180 of this invention is typically formed out of aseptic components. This means that the components of the power module 180, including the components forming the module shell or housing, are not able to withstand the sterilization process to which the handpiece 40 can be exposed.

The power module 180, now described with reference to FIGS. 6-14, includes a base 182 and a cap 204 that, when assembled together collectively form the housing or shell of the module. Base 182 is rectangular in shape. The base 182 includes a bottom plate 184. Opposed side panels 186 extend upwardly along the proximally to distally extending sides of the base. A front panel 188 extends upwardly from the distal end of plate 184 between the side panels 186. A back panel 190 extends upwardly from the proximal end of plate 184 between the side panels 186.

A U-shaped bar 198 with a semicircular bend in the middle is pivotally mounted to the outer face of bottom plate 184. Bar 198 partially seats in a recess 196 formed in the outer surface of the bottom plate 184. Bar 198 functions as a handle to facilitate the insertion and removal of the power module 180 to and from the handpiece 40.

Cap 204 includes a rectangular lid 206. Lid 206 is dimensioned to seat over the open end of base 182. Lid 206 is formed to have openings 208 located along the proximal edge. Posts 209 (two identified) extend downwardly from lid 206. A rim 207 forms the outer perimeter of the lid. Rim 207 is the portion of the lid that actually abuts the top end of base 182.

The cap 204 is further formed to have a tower 210 that extends upwardly from lid 206. The tower 210 subtends a cross sectional area, in planes perpendicular to the top-to-bottom longitudinal axis of the power module, that is less than the area subtended by base 184 and lid 206. The cap 204 is formed so that the tower 210 does not extend from the center of lid 206. Instead, the tower 210 is located towards the distal front end of the lid 206. Cap 204 is formed so that tower 210 has a primary section 212. Tower primary section 212 has a shape that in cross section, in a plane perpendicular to the plane of FIG. 9, can be described as approximately rectangular with rounded corners. Tower primary section 212 occupies approximately 55 to 70% of the total length of the tower 210.

The topmost portion of the tower 210, the portion above the primary section 212, is head 214. The side and rear longitudinal panels of head 214 are recessed inwardly relative to the adjacent side and rear panels of the tower primary section 212. The top of head 214 is formed with a downwardly extending bore 216. Bore 216 has a diameter that is dimensioned to receive the handpiece input spindle 124 so the input spindle can freely rotate in the bore. A slot 218 extends downwardly along the proximally directed panel of head 214. Slot 218 opens into bore 216.

Tower 210 is further formed to have two outwardly protruding ribs. A first rib, rib 226, extends proximally outward from the proximal panel of the tower primary section 212. Rib 226 extends up from lid 206 approximately 40 to 60% of the total length of the tower primary section 212. The second rib, rib 228, extends distally forward from both the primary section 212 and head 214 of the tower 210. Rib 228 extends upwardly from lid 206 and extends along the whole of the length of the tower primary section 212. Rib 228 extends over approximately the bottom 20 to 30% of the tower head 214.

Tower 210 is further formed so that the distally directed panel 227 of the tower, the panel located above rib 226, is located proximally relative to the distal edges of the side panel of the tower (side panels not identified). Panel 227 and the adjacent portions of the side panels that extend forward of panel 227 define a recess 229 in the front of tower 210. A boss 230 extends outwardly from panel 227 into recess 229.

Figure 13:
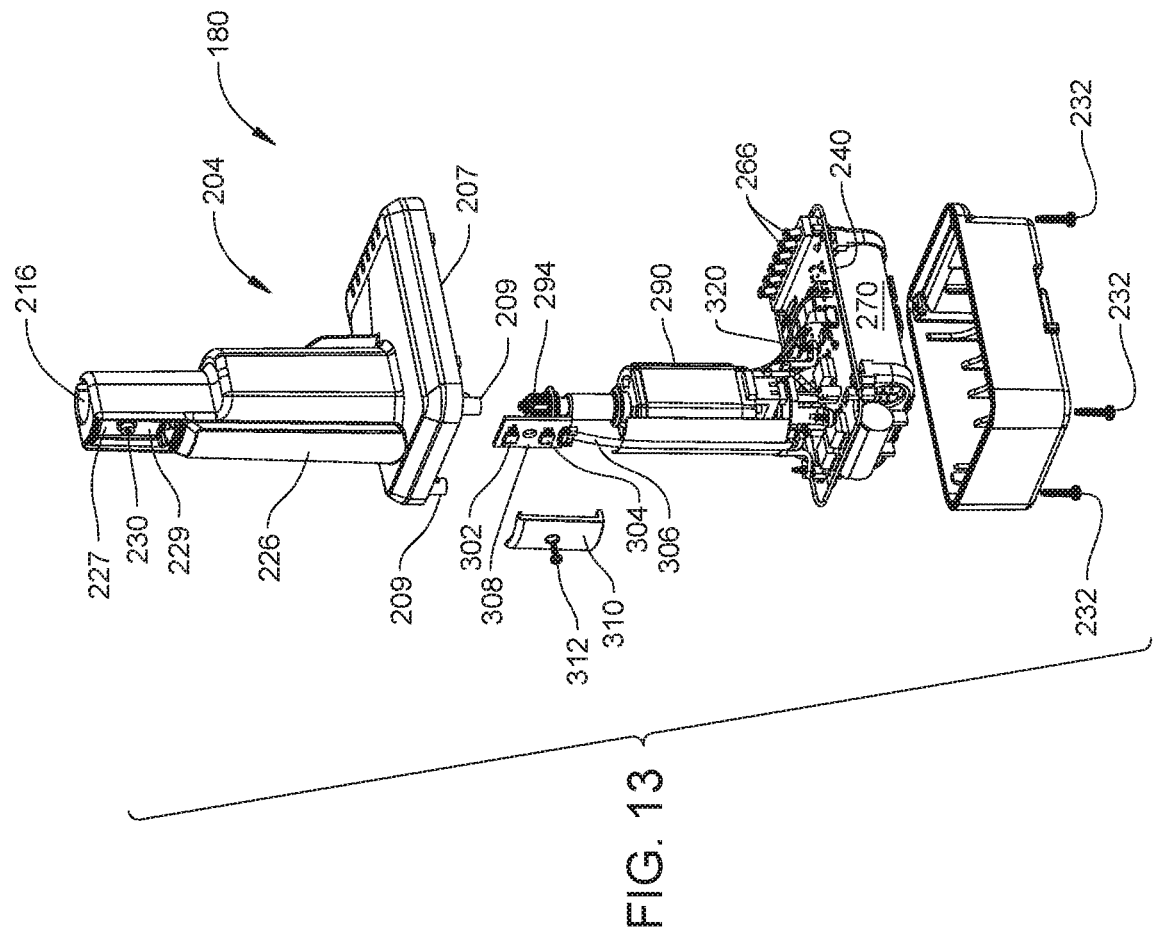
FIG. 13 an exploded view of the components internal to the power module.

Fasteners 232 seen in FIG. 13, secure base 182 and cap 204 together to form the housing or shell of the power module 180. The fasteners 232 extend through openings in the base bottom panel (openings not illustrated) into lid posts 209.

Disposed inside base 182 is a circuit board 240. Circuit board 240 supports the components that form controller 320. Also secured to circuit board are plural contacts 266. When the power module 180 is assembled, contacts 266 are accessible through lid openings 208. Contacts 266 are contacts over which current is sourced to the cells 270 for storage. Contacts 266 also serve as contacts over which data and instructions are written to the controller 320 and over which the controller reads out data.

Secured to the undersurface of the circuit board 240 are cells 270. Cells 270 are rechargeable cells capable of holding a charge. Cells 270 may often be NiCad or Lithium Ion cells. Cells 270 are typically connected together. The type of connections between the cells, serial or parallel, is not part of the present invention. Given that the cells 270 are connected together, the cells are sometimes referred to as a cell cluster.

Figure 15:
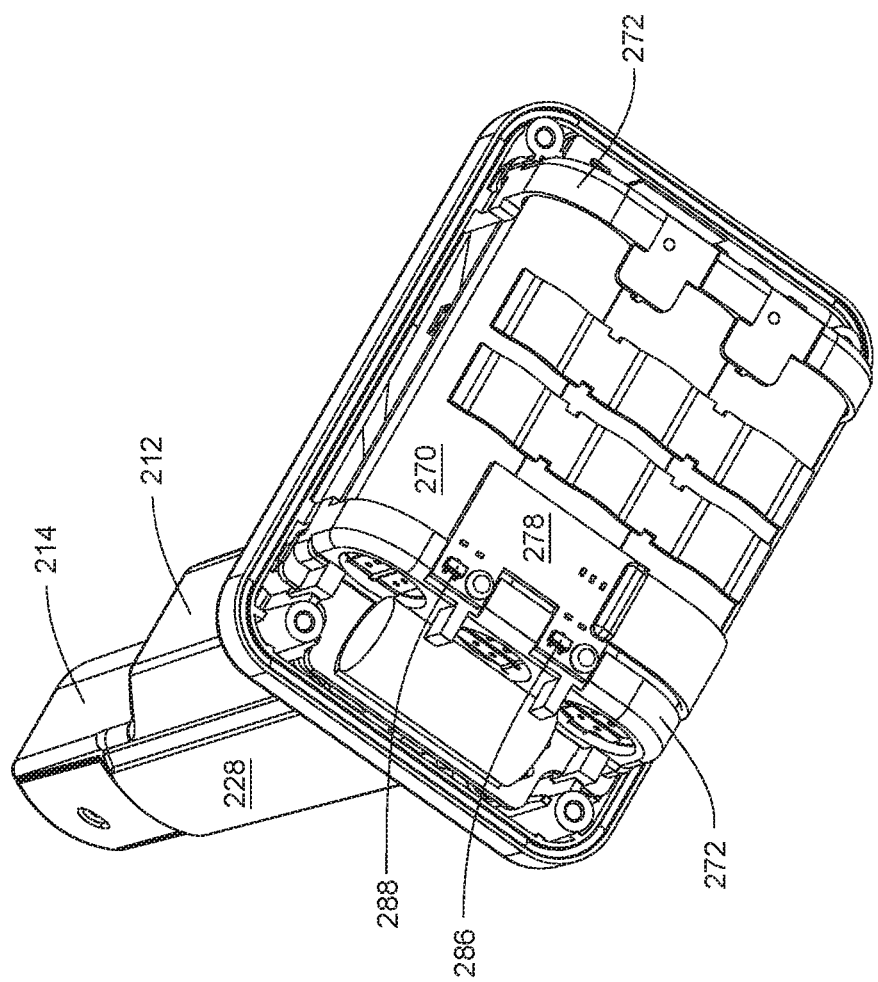
FIG. 15 is a perspective view of how the sensors are mounted to the base of the power module.

From FIG. 15 it can be seen that two U-shaped brackets 272 extend downwardly from circuit board 240. Brackets 272 suspend cells to the undersurface of the circuit board 240.

A circuit board 278 is secured to the bottom surface of the distally located bracket 272. Circuit board 278 has an exposed surface that is directed to the inner surface of power module bottom plate 184. Two sensors 286 and 288 are mounted to the exposed surface of circuit board 278. Sensors 286 and 288 are able to detect the presence/absence of localized magnetic fields. In one version of the invention, sensors 286 and 288 are each a Hall sensor. Tool 30 of this invention is constructed so that sensors 286 and 288 are positioned so that when latch knob 90 is in the fully latched position, each sensor 286 and 288 is located immediately above a separate one of the bores 97 formed in the latch knob.

Returning to FIGS. 13 and 14, it can be seen that power module motor 290 is also mounted to the upper surface of the circuit board 240. The motor 290 is mounted in the cap tower 210. An output shaft 294 is connected to the motor rotor to rotate upon rotation of the motor rotor. Power module 180 is constructed so that the free end, the head, of the output shaft 294 is disposed in tower bore 216. The head of output shaft 294 is formed with features that facilitate the releasable engagement of the shaft 294 with the handpiece input spindle 124. In the illustrated version of the invention the engagement features are teeth (not identified).

The power module 180 includes two additional sensors, sensors 302 and 304 that are disposed in recess 229. Sensors 302 and 304 are configured to monitor the actuation of triggers 152 and 154. In the described version of the invention, sensors 302 and 304 are Hall effect sensors. Sensors 302 and 304 are mounted to a circuit board 308 seated in recess 229. A ribbon cable 306 extends from circuit board 240 to circuit board 308. Cable 306 includes the individual conductors (not illustrated) that establish the electrical connections required to connect sensors 302 and 304 to the other control components integral with the power module 180. Cable 306 extends through the opening between recess 229 and the void internal to tower 210.

When the power module 180 is assembled, the circuit board 308 is seated in the tower recess 229 so the circuit board seats over boss 230. Not identified is the hole in the circuit board 308 in which boss 230 is seated. A plate 310 formed from magnetically permeable material such as a plastic polymer is seated over the tower recess 229. A threaded fastener 312 extends through an opening in plate 310, the hole in the circuit board and into the tower boss 230. Fastener 312 holds both circuit board 308 and plate 310 to the tower 210.

Figure 16:
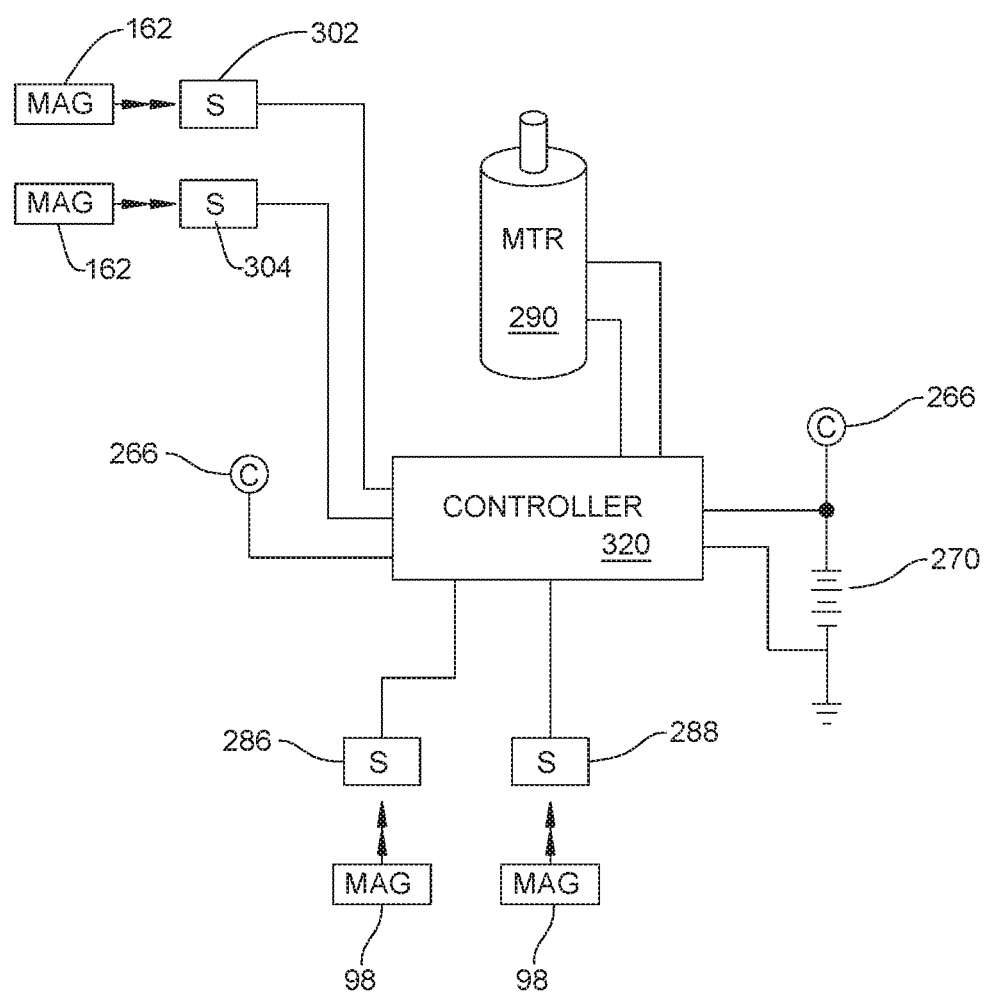
FIG. 16 is a block diagram of the electrical circuit of the power module.

FIG. 16 provides a view of the fundamental components of power module that control the actuation of motor 290. Specifically, mounted to circuit board 240 is the controller 320. Controller 320 selectively ties the windings of motor 290 to either the positive or negative terminals of the cluster of cells 270 to cause the actuation of the motor. In FIG. 16 the controller 320 is shown as a single block component. This is for purposes of illustration only. It should be understood that the controller 320 typically includes plural components. Typically, these components include: a signal processor that includes a memory with preloaded instructions; and switching components that selectively tie the cells 270 to the power generating unit, motor 290. As discussed below though, it should be understood that the controller is able to: receive signals indicating the specific type of handpiece to which the power module is attached; and, based on the handpiece type signals, cause the motor to run in a state that is appropriate for that handpiece. One such controller that comprises a number of different components is disclosed in the incorporated by reference U.S. Pat. No. 7,638,958/PCT Pub. No WO 2007/002180. The controller of this document includes a digital signal processor able to regulate motor operation based on a set of instructions loaded in the processor memory. This controller so includes a set of high voltage drivers. The drivers selectively tie the windings of the motor to either the positive or ground terminals of the cluster of cells 270.

As inputs, controller 320 receives the signals output by the handpiece detect sensors 286 and 288. Controller 320 also receives the signals asserted by the trigger state sensors 302 and 304. While not illustrated, it should be understood a bias current is applied to each of sensors 286, 288 302 and 304. Controller 320 regulates the application of the bias currents to the sensors.

Controller 320 is not connected to cluster of cells 270 to regulate the application of current to the motor 290. The controller 320 is also connected to the cells 270 to receive current from cells. This is the current that energizes the electrically active components of the controller 320.

Cells 270 is shown as being connected to a single contact 266. This to represent that current is sourced to the cells through the contacts 266. Controller 320 is also shown as being connected to a single contact 266. This to represent that instructions are written to the controller 320 and data are written out of the controller through the contacts 266.

IV. Operation

The operation of tool 30 of this invention begins with the sterilization of the handpiece 40 and charging of the power module 180. The means by which the handpiece 40 is sterilized is not part of the present invention. Generally, though a process by which a surgical tool can be sterilized to the appropriate sterilization assurance level may be employed. The handpiece 40 may be subjected to an autoclave sterilization process. Alternatively, the handpiece may be exposed sterilants other than steam. These sterilants include vaporized hydrogen peroxide or vaporized ethylene oxide.

Power module 180 is charged by placing the module in a charger able to source current to the cells 270. The current is sourced from the charger by contacts integral with the charger that are connected to power module contacts 266.

Figure 17A:
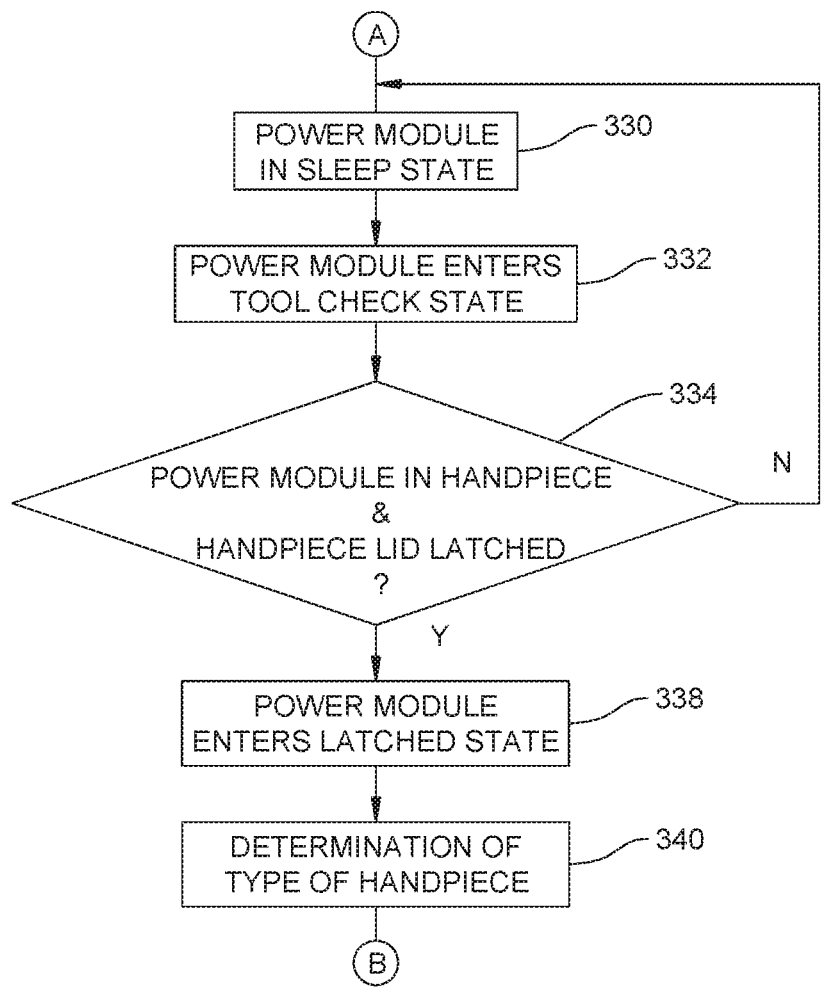
FIGS. 17A and 17B form a flow chart of the operation of the tool of this invention.

Absent any other event, the power module is normally in a sleep state as represented by step 330 of FIG. 17A. When the power module is in the sleep state, the controller is a lower power mode. This means only the components required to maintain the power module 180 in this mode are energized. Thus, when the power module is in the sleep state, bias currents are not applied to the sensors 286, 288, 302 and 304. Other components that may not be energized when the power module 180 is in the sleep state are driver circuits that tie the motor windings to the terminals of the cell cluster. When controller 320 is in the sleep state, the controller draws the smallest amount of current of the power module operating states.

When the controller is in the sleep state it periodically wakes up and enters a tool check state, step 332. When the controller 320 enters the tool check state the controller applies the bias currents to sensors 286 and 288 needed to activate these sensors. Signal processing components internal to the controller 320 needed to evaluate the signals from sensors 286 and 288 are also turned on. It should thus be appreciated when the controller is in the tool check state, the controller draws more current than when in the sleep state.

When controller 320 is in the tool check state, the controller monitors the signals output by sensors 286 and 288. If the power module has not been placed in a handpiece 40 and the handpiece lid has not been properly latched, there should not be magnetic fields in the vicinity of either sensor 286 or sensor 288. The signals output by sensor 286 and 288 indicate that no such fields are present. Step 334 represents the controller evaluating the signals from sensors 286 and 288.

If the evaluation of step 334 tests negative, no magnetic fields detected adjacent either sensor 286 or 288, controller 320 interprets these data is indicating that the power module has not been properly coupled to a handpiece 40. As represented by the loop back to step 330, the controller 330 returns the sleep state. The application of the bias currents to the sensors 286 and 288 is negated.

In some versions of the invention, the controller 320 transitions from the sleep state to the tool check state once every 100 to 500 milliseconds. Each time the controller 320 enters the tool check state, the controller stays in the state approximately 5 to 10 milliseconds.

To continue the process of configuring a tool of this invention for use, the power module 180 is inserted in the handpiece 42. The shell handgrip 46 is asymmetrically located relative to the shell base 44. The power module tower 210 is asymmetrically located relative to the module base 182. Owing to the asymmetry of these components, the individual inserting the power module in the shell inherently tends to inserts the power module in the shell in the correct orientation.

Upon inserting the power module 180 in the handpiece, the arcuate portion of bar 198 seats in lid recess 69

As a result of the insertion of the power module 180 in the shell 42, the head of module output shaft 294 engages base 126 of the handpiece input spindle 124. Also, at this time, sensor 302 enters into a position in which the sensor is in close proximity to trigger magnet 162. Sensor 304 enters into a position in which the sensor is close proximity to trigger magnet 164.

Lid 62 is then rotated closed over the open end of shell base 44. The arc around which lid 62 is rotated is limited by the abutment of the plate tab 88 against the opposed surfaces of the lid that define the sides of the space above step 92. When the lid 62 is in the fully unlatched state, a toe 87 integral with one of the beams 86 seats in the adjacent detest. When the lid is in the fully latched state, the toe 87 integral with the other beam seat in the second detent. The changes in the resistance to the rotation of the lid as a result of the seating/unseating of the toes 87 in detents 92 provides a tactile indication of the latched/unlatched state of the lid 64. The rotating of latch knob 90 to the latched position completes the process of coupling the power module to the handpiece. As a consequence of the rotation of the latch plate lip 103, the lip presses against the adjacent lip of the shell base. Owing to the dimensioning of the components, lip 103 of latch plate 102 rotates into slot 45 formed in the handpiece shell base 44. Owing to the rotation of the tapered surface of lip 103 against the adjacent surface of the shell base that defines slot 45, the rotation of the latch plate drives the lid against the shell base. More particularly, the perimeter of the gasket 73, the portion of the gasket that extends outwardly from plate 79, is driven against the bottom edge surface of the shell rim that defined the open end of the shell base 44. The compression of gasket 73 seals the power module 180 in the handpiece shell 42. Gasket ribs 74 press against the undersurface of the base of the power module. Gasket ribs 74 thus function as a shock absorbers that prevent the movement of the power module 180 in shell compartment 52.

The rotation of latch knob 90 to the fully latched state also places a first one of the lid magnets 98 in close proximity to power module sensor 286. The second lid magnet 98 placed in registration with power module sensor 288. Here the "fully latched" state is understood to be when the latch 62 is positioned to, as completely as designed, prevent the unintended opening of the lid 62. Accordingly, the next time the evaluation of the tool check state is performed, sensors 286 and 288 each assert a signal indicating that a local magnetic field has been detected. Controller 320 interprets the signal that even one magnet field is detected as indication that the power module has been seated in the shell compartment and the lid 62 is fully latched. Controller 320 therefore places the power module 180 in the latched state, step 338.

Upon placing the power module 180 in the latched state, the controller 320 initially determines the type of handpiece to which the power module is attached. This determination, in step 340, is made by determining which one of the sensors is asserting a signal indicating the close presence of a magnet. There are three possible conditions: only sensor 286 senses a magnetic; only sensor 288 senses a magnet; or both sensors 286 and 288 sense the presence of a magnet. Thus in this version of the invention, in step 340, controller 320 determines to which one of three possible handpieces the power module 180 is connected.

Based on the determination of step 340, in a step 342, the controller configures the power module for operation. This may include selecting from preloaded data the following operating characteristics of the motor: a maximum rotor speed; or current draw. Thus for the rotary handpiece 40, the controller may configure the power module so when a trigger is depressed a maximum amount the motor will run at a maximum speed of 25,000 RPM. In step 342 the controller also configures the power module how to operate as a function of the depression of one or both of the triggers. For example for a first type of handpiece, it may be appropriate to configure the module so that an indication that trigger 152 was depressed in an indication that the motor should run in a forward direction and an indication that trigger 154 was depressed an indication that the motor should run in a reverse direction. For a second type of handpiece an indication that trigger 152 was depressed would again serve as an indication that motor should run in the forward direction. For the second handpiece an indication that trigger 154 was depressed serves as indication the motor should be run in an oscillatory pattern.

Once controller 320 finishes configuring the module, the controller causes the module to enter an active state, step 346. In the active state, the controller sourcing bias current to sensors 302 and 304. Also, voltages are applied to all components internal to the module that need to be turned on in order to actuate the motor 290. When power module 180 is in the active state, the controller draws more current than when in the tool check state. As represented by step 348, when the power module 180 is in the active state, the controller 340 waits to determine if one of the triggers 152 or 154 has been depressed. This monitoring is performed monitoring the signals output by sensors 302 and 304.

Once the power module 180 is in the active state, handpiece 30 is ready for use. Prior to this time the appropriate front end attachment and device driven by the handpiece are typically attached to the handpiece 40. Tool 30 is actuated by the depression of the appropriate trigger 152 or 154. This causes the associated magnet 162 or 164, respectively, to move towards the adjacent sensor 302 or 304, respectively. Sensors 302 and 304 output sensor signals representative of the extent to which the associated magnets are depressed. Based on these signals and the previously loaded handpiece type configuration instructions, the controller actuates the motor, step 354, to cause the movement desired by the practitioner.

While the motor 270 is actuated, the power module controller continually monitors the sensors 302 or 304, step 356. This monitoring is performed to determine if the trigger 152 or 154 was released. The release of one of the depressed trigger 152 or 154, results in the change of the output signal from the associated sensor, 302 or 304, respectively. In response to this change in the sensor signal, controller 320, in step 358 deactivates the motor. The controller then returns to step 348 to await the next depression of the trigger.

Figure 17B:
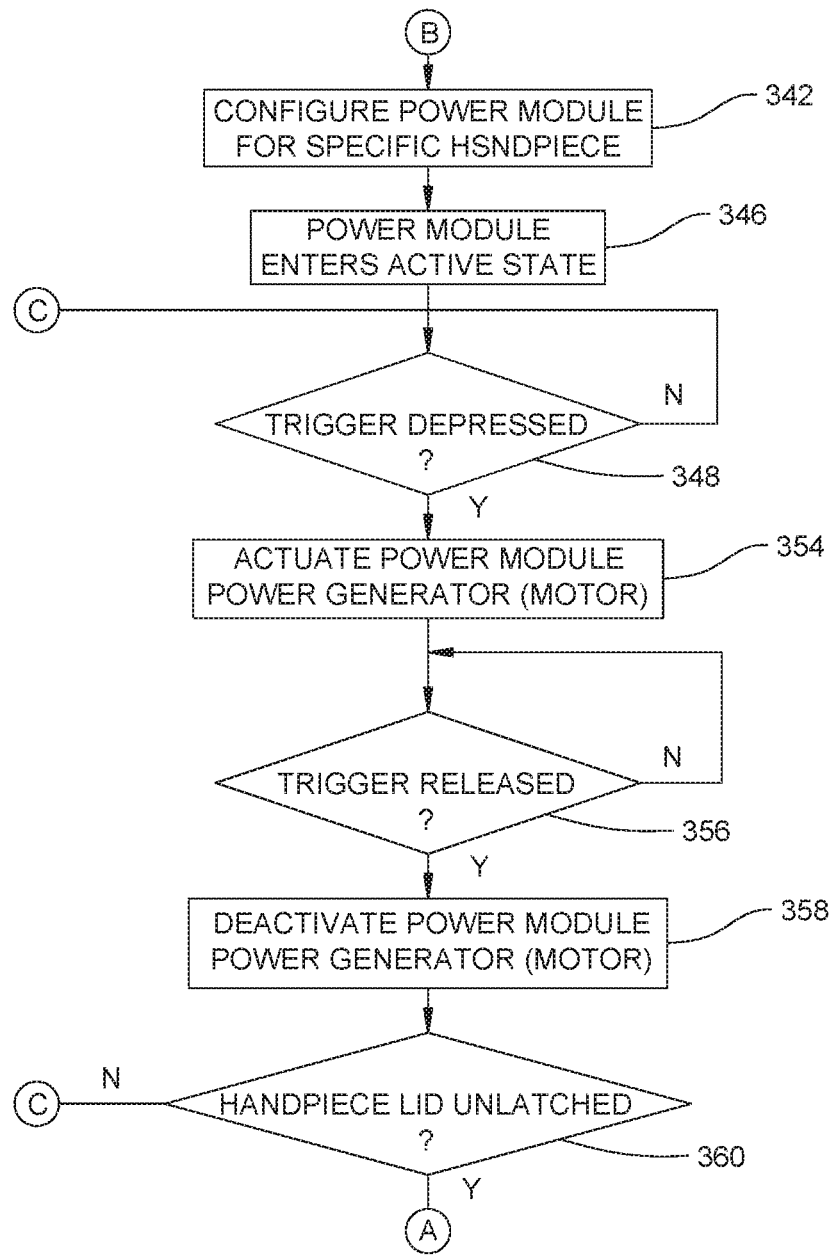

Once the controller enters the tool check state, the controller continually monitors sensors 286 and 288 determine if the signals asserted by these sensors change. In FIG. 17B, for ease of illustration, this is shown as a separate step 360 occurring after step 358 is executed. Step 360 is essentially identical to step 334. This monitoring is performed because, at some time, the latch may rotate away from the fully latched state. Ideally, this event should only occur when the motor 290 is in a deactivated state.

If, in step 360 the processor determines the change of the signals indicate that the latch is moving away from the fully latched state and the motor is active, controller 320 initially deactivates the motor (step not shown). Regardless of whether or not the motor is running when the latch is opened, the controller then returns the power module to the sleep state, step 330. Then, as described above, steps 332 and 334 are cyclically reexcuted to determine whether or not the power module 180 is properly latched in a handpiece.

V. Operation with a Different Handpiece

Figure 18:
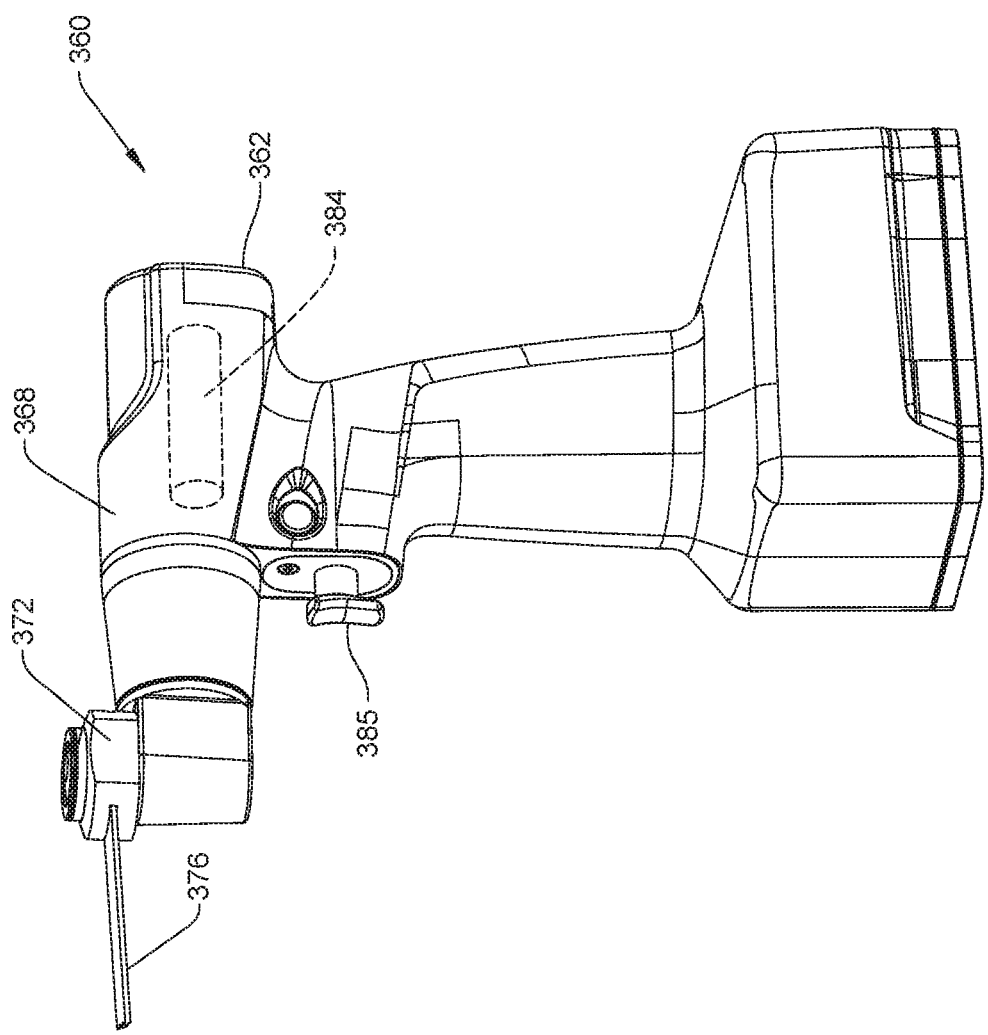
FIG. 18 is a perspective view of an alternative handpiece that forma a tool of this invention.

An alternative handpiece 360 that can be employed as the handpiece of tool 30 of this invention is seen in FIG. 18. Handpiece 360 includes a shell 362 with a base 364, a handgrip 366 and a barrel 368. Base 364, handgrip 366 and barrel 368 are similar in shape and function to, respectively, the previously described base 44, handgrip 346 and barrel 48. A head 370 extends forward from the distal end of the barrel 368. A blade mount 372 is rotatably mounted to the head 370. Blade mount 374 is configured to releasably hold a sagittal saw blade 376. Blade 376 is understood to be the energy applicator used with handpiece 360.

Internal to barrel 368 is a transmission assembly. This transmission assembly is represented as a cylindrical phantom shaft 384. The transmission assembly converts the rotary motion of the power module output shaft into a motion that pivots the blade mount 372 around an axis. This axis is perpendicular to the proximal-to-distal longitudinal axis through the barrel 368. Since blade 376 is pivotally mounted to the blade mount the pivoting of the blade mount results in a like back and forth motion of the blade 376. The blade teeth thus reciprocate back and forth along an arc located forward of the handpiece.

Handpiece 360 has a single trigger 385. Trigger 385 is analogous to trigger 154.

A lid 388 is hingedly secured to the open bottom end of shell base 364. Lid 364 is essentially identical to previously described lid 62. To avoid redundancy the components integral with lid 388 are not illustrated. There is one significant difference between lids 62 and 364. Only a single magnet 98 is mounted to the latch knob 90 of 364. Arbitrarily the magnet 98 mounted to lid 364 is the magnet the presence or which is sensed by sensor 288.

A tool 30 of this invention that includes handpiece 360 is prepared for use the same way a tool with handpiece 40 is prepared for use. After handpiece lid 388 is placed in the full latched state, in step 340 only sensor 288 outputs a signal indicating that a magnet was detected. In response to receipt of this signal magnet detected signal from sensor 288, the controller 320 recognizes that the attached handpiece type is of the type that includes sagittal saws.

Consequently, in step 342, the controller configured the tool for operation based on this type of handpiece. Thus, in this version of the invention, this means the controller configures the handpiece to operate so when the trigger is fully depressed the maximum speed at which the handpiece will run the motor is 20,000 RPM. This is different from the maximum speed at which the controller 320 will run the motor than when handpiece 40 is detected.

Tool system 30 of this invention is thus configured so that upon the latching of the power module 180 in a handpiece 40 or 360, the module controller 320 determines that the power module 180 is both properly latched in place and the type of handpiece in which the module is seated. Based on this later information the controller configures the power module to operate correctly for that type of handpiece. This invention thus eliminates the need for an individual to manual set the power module to the correct operational setting for the type of handpiece. This invention does more than eliminate the time required to perform this task. The invention eliminates the likelihood that due to error the handpiece type data are incorrectly entered.

Still another version of this specific version of the invention is that the data tag, the set of magnets, does more than provide an indication of handpiece. The absence/presence of this magnets serves as an indication whether or not the lid is properly latched.

It is a further feature of this invention that the sensors 286 and 288 that detect the proximity of the handpiece lid 62 and the trigger sensors 302 and 304 are spaced at least 5 cm apart and more preferably at least 8 cm apart. This feature of the invention reduces the likelihood that if a single magnet is somehow placed adjacent the power module that this single magnet will cause fields to be detected by both sets of sensors. If this event was to occur, it could result in the unintended actuation of the power module.

Further some tools, as a very nature of their operation, undergo a high degree of vibration. Under some circumstances, this vibration could cause the latch to move away from the fully latched state. As described above with reference to step 360, the tool system of this invention is further configured to continuously monitor whether or not the latch is in the fully latched state. The termination of the activation of the power generating unit or the inability to turn on the tool provides a cue to the user that the latch may have moved from the fully latched state. This provides the surgical personnel the opportunity to withdraw the tool from the sterile field verify the lid is latched or relatch the lid 62. This substantially reduces the likelihood that, as a result of the latch unlatching, the lid opens and the module falls out handpiece. If this event were to occur in close proximity to the patient the power module could contaminate the sterile field.

Still other advantages of tool 30 of this invention are associated with how the components forming the system are manufactured. In the described version of the invention, the cells 270 are in parallel. Each cell 270 is centered on a longitudinal axis that is perpendicular to the longitudinal axis of the tower 210 and motor 290. Often the tower 210 and motor 290 have a common longitudinal axis. Further the cells 270 project outwardly beyond the tower 210. This construction of the invention provides the module base 182 with a center of mass that is closer to the module bottom plate 184 than the head 214. This provides the module with stability when placed on a surface. By extension this feature of the module as well as the module 180 serves to stabilize the tool 30 when the module 180 is in the handpiece 40 or 360 and resting of the tool lid 62.

A further feature of this invention is that both the contacts 266 over which a charging current are applied to the cells 270 and the cells themselves are disposed in the module base 182. A benefit of this feature of the invention is the conductors over which the relatively high charging currents are sources from the contacts 266 to the cells 270 only have to extend through the module base 182. There is no need go to the expense of routing these contacts, through which charging current flows, through the module tower 210.

Still a further feature of this invention is that contacts 266, cells 270, sensors 286 and 288 and controller 320 are mounted to a common circuit board 240. A benefit of this feature of this invention is that once these components are mounted to the circuit board 240, the circuit board can be fitted to the power module 180. This construction facilitates the economical assembly of the power module.

VI. Maintenance Key

Figure 19:
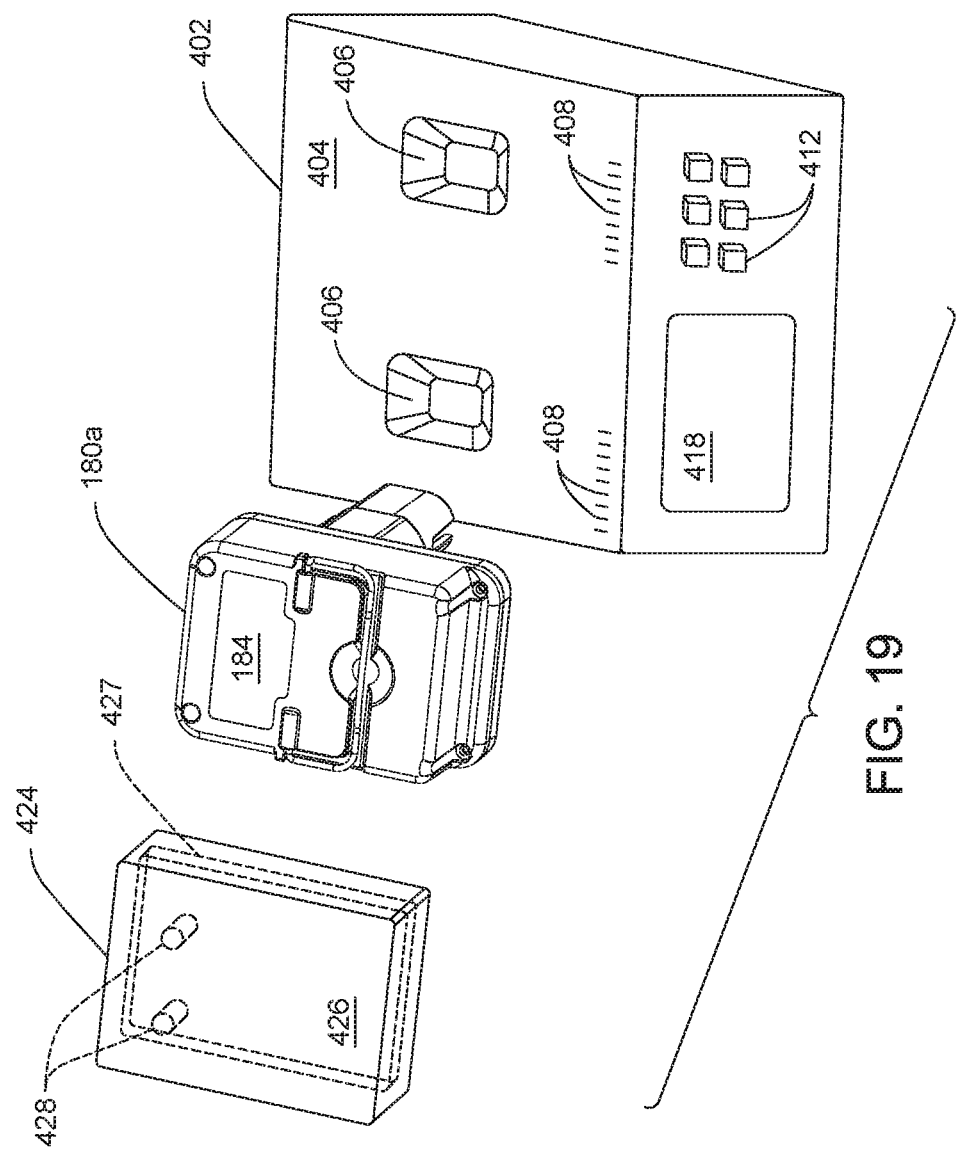
FIG. 19 is exploded view of how a key can be fitted to the power module to place the module in a maintenance mode.

FIG. 19 depicts how a maintenance key 424 can be fitted to a power module 180*a* to place the power module in a maintenance mode. In FIG. 19 the power module 120 is shown as being coupled to a charger 402. Charger 402 includes a shell 404 in which the internal components of the charger are housed. The shell 404 is formed with a bore 406 dimensioned to accommodate the power module tower 210. The specific charger 402 is designed to charge two power modules 180. Shell 404 is therefore formed with two bores 406. Two sets of contacts 408 extend upwardly from the top surface of the shell 404. When a power module 180*a* is seated on the charger 402 such that the module tower is disposed in a bore 406, the charger contacts 408 extend through the openings 208 in the power module lid 206. The charger contacts 408 engage the power module contacts 206 to provide the necessary conductive links between the power module 180 and the charger 404.

Not illustrated and not part of the present invention are the components internal to the charger that source current to the cells 270 and provide other functions some of which are described below. These other components include a power supply, a load resistor and a processor. The components inside chargers are disclosed in U.S. Pat. Nos. 6,018,227 and 6,564,242, each of which is incorporated herein by reference. Seen on the outside of the shell are buttons 412 and a display 418. Buttons 412 are the control members that are depressed to control the charging process. Display 418 is the component of the charger 402 on which images are presented that provide information about the charging process and the state of the power module 180*a*.

The maintenance key 424 is a component that is placed on the power module 180 when the power module is attached to the charger 402. The maintenance key 424 is placed on the power module when the person handling the power module wants to do more than simply recharge the cells. The body of maintenance key 424 is a plate 426 designed to extend over at least some of if not all of the power module bottom plate. A rim 427, the portion of the maintenance key below the dashed line, extends downwardly from and circumferentially around the outer perimeter of key plate 426. Rim 427 extends around the outside of the power module side, front and back panels 186, 88, and 190, respectively, so as to removably hold the key 42 static to the power module 180*a*.

Internal to the plate 426 are two magnets 428, represented by phantom cylinders. Magnets 428 are positioned so that when key 424 is seated over the power module 180 one magnet is disposed over sensor 286 and the second magnet is disposed over sensor 288.

A power module 180*a* is identical in structure to previously described power module 180. Power module 180*a* of this version of the invention has four operating states. The first state is when neither sensor 286 nor sensor 288 assert a signal indicating the presence of a nearby magnet. When this condition exists, controller 320 recognizes that the power module is being in the state in which the module is not in a fully latched handpiece. The second and third states are when just one of the sensors 286 or 288 asserts a signal indicating a magnet is nearby. When this condition exists the controller 320 recognizes the power module as being in a fully latched handpiece and connected to either a first type of handpiece (the second or a second type of handpiece (the third state).

The fourth state is when the sensors 286 and 288 assert signals indicating that a magnet is adjacent both sensors. The power module 180*a* is in this state only when key 424 is fitted over the module base 184. When this condition exists, the controller 320 recognizes the power module 180*a* is being in a maintenance state. When power module 180*a* is in the maintenance state, the controller writes out to the charger 42, information regarding the operating history of the module.

Power module 180*a* operates in the same general manner in which power module 180 operates as described with reference to FIGS. 17A and 17B. When the power module 180*a* is placed on the charger 402 the placing of the key 424 on the module bottom plate 184, in step 334, cause the controller to initially interpret the module as being in a handpiece that is fully latched. In the evaluation of step 340 the controller 320, based on the signals from both sensors 286 and 288 recognizes that the module is not in a handpiece but has rather been placed in a maintenance mode.

Once the power module 180 recognizes that the module is not in a handpiece, steps 342-360 are not executed. Instead, the controller 320 writes out the data stored in the memory integral with the memory. These data are written out to the processor integral with the charger 402 using a process not part of the present invention. These data depending on the structure of the charger may be available for presentation on the display 412 or for storage in a device remote from the charger 402.

A benefit of the above arrangement is that it provides a means to place the power module 180*a* in the maintenance mode without requiring the entry of special data.

Once in the maintenance mode data can, if necessary, be uploaded into the power module controller 320. These data include updated instructions for controlling the operation of the module power generating unit.

VII. Alternative Embodiments

The above is directed to specific versions of the invention. Alternative versions of the invention may have features different from what is described above.

It should be understood that for one or more specific types of handpieces there are several sub-types of the handpiece. Thus a single trigger saw type handpiece may include both a saw that is a sagittal saw and a second saw, a reciprocating saw.

For example, there is no requirement that in all versions of the invention magnets function as the data tags that indicate the type of handpiece to which the power module is connected. In one alternative version of the invention, the data tag integral with the handpiece are RFID tags. In this version of the invention, the data reader is a circuit integral with the power module capable of reading the RFID tags. Collectively, these components are mounted so that the reader can only read the REID tag when the handpiece latch is in the locked state. In this version of the invention, when the power module is in the tool check state, the controller integral with the module temporarily actuates the RFID reader. The reader broadcasts an basic interrogation signal and waits for response. The absence of a response to this basic interrogation signal is interpreted as an indication that the power module is not seated in a handpiece with a properly latched lid. A response to the basic interrogation signal is interpreted by the controller as an indication that the power module is disposed in a properly latched handpiece. If the tool system is in this state, the power module controller causes the data in the REID tag to be read out. These data include the handpiece type data used in step 342 to configure the tool for the specific handpiece type.

In some other versions of the invention, the data tag is a bar code. In these versions of the invention the reader is a device integral with the power module capable of reading the bar code. In still other versions of the invention, the data tag is a NOVRAM or EEPROM. In these versions of the invention, the data reader may include contacts integral with the power module. These contacts come into contact with complementary contacts integral with the handpiece that are connected to the NOVRAM or EEPROM. In these versions of the invention, the process of determining whether or not the power module is in a properly latched handpiece and the type of handpiece similar to the steps described above with respect to when the data tag is an RFID tag.

In some versions of the invention, the components used to determine whether or not the power module is in a fully latched handpiece and the data tag/data reader are separate from each other. For example, in one embodiment of this version of the invention, a magnet mounted to the latch may serve as the component that is sensed to determine whether or not the power module is in a handpiece that has been properly latched. In this version of the invention, another component such as an RFID tag or bar code functions as the data tag.

In still another version or this invention a single magnet serves both as the data tag and the component that indicates whether or not the power module is seated in a properly latched handpiece. In these versions of the invention, the sensor that monitors the strength of the sensed magnetic field generates a signal that varies as a function of the magnitude of the magnetic field. In this version of the invention, a single magnet is mounted to the handpiece. The strength of the magnet is selected as a function of the type of handpiece. In this version of the invention, the controller interprets a signal from the sensor indicating that a magnetic field is present as an indication that the power module is contained in a properly latched handpiece. The controller then determines the type of the handpiece based on the strength of the magnetic field.

In other versions of the invention in which plural magnets function as the data tag, the handpiece may have more than two magnets. For example, in some versions of the invention, the handpiece may have up to four magnets that are employed to indicate handpiece type. In this version of the invention, the power module data reader would consists of sensors able to determine the presence/absence of each of these magnets. Thus in this version of the invention, assuming the magnets also provide the data indicating whether or not the lid is properly latched, this version of the invention could provide data indicating which one of up to 15 different types of handpieces is coupled to the power module. In this version of the invention, each of the magnets may not be on lid knob. In this version of the invention, two or the magnets may be attached to the lid knob. The remaining magnets are, if present, attached to the lid. Thus, in this version of the invention, the presence/absence of the lid knob-mounted magnets are attached to the lid knob are used to provide an indication of both the lid being latched and some data regarding handpiece type. The presence/absence of the remaining magnets are used to provide the rest of the handpiece-type data.

It should likewise be understood that the power generating unit may be different from the described motor. Thus in some versions of the invention, the power generating unit may be device that outputs an RF signal. In these versions of the invention, the handpiece includes an electrode that services the conductive member over which the RF signal is applied to a site on the patent. Based on the data tag associated with the handpiece, the controller integral with this power module may set one or more of the following characteristics of the RF signal; frequency; pulse duty cycle; voltage; current; or waveform shape.

In other version of the invention, the power generating unit is a transducer that vibrates. In these versions of the invention, the handpiece includes a tip. The tip is the component of the tool through which the vibrations of the transducer are applied to tissue. In these versions of the invention, based on the handpiece type data, the controller integral with the power module is able to set at least one of the following: frequency of transducer vibrations; duty cycle of vibrations; or voltage and current of the drive signal applied to the transducer.

Other power modules may include power generating units that emit heat (thermal energy) or light (photonic) energy. Each of these different power modules can be used with different, plural types of handpieces. Each handpiece has specific type of applicator that is used to apply the energy to tissue in order to accomplish a specific medical or surgical task.

Similarly, there no requirement that all tools of this invention be pistol shaped like illustrated handpieces 40 and 360. In alternative versions of the invention, the handpiece may have elongated pen or pointer like shape. In other versions of the invention, the geometric features with which the handpiece and power module are provided to ensure that these components are properly aligned may differ from what has been described. Thus in one version of the invention, the handpiece shell and the power module may both be generally cylindrical in shape. In this version of the invention, the interior of the handpiece shell or housing may have a single rib or groove. The associated power module shell is formed with a complementary groove that accommodates the rib or a complementary rib that seats in the groove.

The components integral with different versions of the invention may have features different from what has been described. For example, in some versions of the invention, the latch, instead of rotating may move longitudinally. In versions of the invention where it is critical to sense the presence/strength of magnetic fields sensors other than Hall sensors may be employed. These sensors include reed switches.

Likewise other sensing assemblies may be incorporated into alternative versions of the invention to determine whether or not the user actuated control member has been depressed. For example, in some versions of the invention, internal to the power module is a variable resistor. The wiper that sets the resistance is set by the control member integral with the handpiece.

In versions of the invention wherein the trigger displaces a magnet, there may be two sensors associated with each magnet. In these versions of the invention, the sensors may serve a redundancy purpose. Alternatively, in these versions of the invention, the power module is configured to when in the latched state, activate the low powered one of the sensors. When the signal from this sensor indicates the associated trigger was depressed, the controller places the power module then enters the active state. When the power module is in the active state, the higher power-consuming sensor is actuated. The signal from this second sensor is what causes the controller 320 to selectively actuate the handpiece power generating unit.

Also, it is within the scope of this invention, that the handpiece be constructed of components that can be sterilized upon manufacture but not resterilized. This handpiece may be useful in the event manufacturing economics make it less costly to provide a use once handpiece than a handpiece formed out of components that must be able to withstand the rigors of the sterilization process.

Likewise the process steps executed by other versions of this invention may differ from what has been described. For example, there may be a version of this invention where the control components will not over an extended period of time of several days or more appreciably drawn down the charge in the cells. In this version of the invention it may not be necessary to conserve power by cycling the power module between a power saving sleep state and the other states in which a greater quantity of charge is drawn.

In some versions of the invention the energy applicator that extends from the handpiece may be part of the handpiece. One type of handpiece that would have this structure would be an ultrasonic handpiece. In this type of handpiece, the vibrating tip, may be integrally built into the shell portion of the handpiece. A second type of handpiece that could have this structure is an RF ablation tool. This type of handpiece would thus be constructed so the electrode that serves as the device over which the energy output by the power generator is applied to the tissue is against built into the shell portion of the handpiece. Handpieces of these versions of the invention therefore do not including coupling assemblies that removably hold the energy applicator to the rest of the handpiece.

In some versions of the invention that rely on a key to place the power module in the maintenance mode, the physical key 424 may be only one component that is needed to place the power module in the maintenance mode. In other versions of the invention, processor 320 must determine that plural conditions exist before it places the power module in the maintenance mode. For example, the processor may only place the power module 180*a* in the maintenance mode when the processor determines (1) the power module is attached to the charger 402 and (2) the physical key is in place. Thus, this version of the invention is constructed so the power module will only enter the maintenance mode when the module is attached to a charger 402. Processor 320 makes this determination by monitoring the signal present at one of the contacts 266 integral with the power module 180*a*. This may be the contact 266 over which current is sourced to the cells 270. Alternatively, this may be a contact 266 over which a flag signal or a data signal is received when the power module 180*a* is connected to the charger.

A benefit of this construction of the invention is that ensures that the power module only enters the maintenance mode when the module is attached to the charger. A second benefit of this construction of the invention is that the set of signals that indicate that power module is the maintenance mode can have two functions. Specifically, when the controller 320 receives the signals and without an indication that current is being sourced, the controller can interprets the power module being latched in a specific type of handpiece. When the controller receives the signals with the indication that current is being sourced, the controller can interpret the power module as being attached to the charger and the individual performing the charging wants the power module placed in the maintenance mode.

The features of the various versions of the invention can be combined as necessary.

Thus, it is an object of the appended claims to cover all such variations and modifications that come within the true spirit and scope of this invention.

What is claimed is:

1. A surgical handpiece including:
   a shell defining a void for receiving a power module and an opening through which the power module is inserted into and removed from the void;
   an energy applicator attached to the shell, the energy applicator configured to, when actuated, output energy for application to a tissue to perform a medical/surgical task;
   a transmission component disposed in the shell for transmitting energy output by the power module to the energy applicator;
   a lid moveably mountable to the shell to cover the shell opening;
   a latch moveably attached to one of the shell or the lid for holding the lid in a latched state; and
   a data tag is mounted to the latch so as to move with the latch, the data tag including an element that is used to identify the surgical handpiece.

2. The surgical handpiece of claim 1, wherein:
   the shell has;
      a base,
      a grip that extends upwardly from the base, and
      a barrel disposed over the grip,
   wherein the base and grip define the void and the base has the opening through which the power module is inserted and removed;
   the energy applicator extends forward from the barrel; and
   the lid is moveably attached to the base to cover the shell opening.

3. The surgical handpiece of claim 1, wherein a coupling assembly is mounted to the shell to removably hold the energy applicator to the shell.

4. The surgical handpiece of claim 1, wherein the energy applicator is configured to one of: be rotated; be oscillated; be vibrated; receive and apply RF energy; receive and apply thermal energy; and receive and apply photonic energy.

5. The surgical handpiece of claim 1, wherein the data tag is one from the group consisting of: a set of magnets; an RFID tag; a memory; and a bar code.

6. The surgical handpiece of claim 1, wherein the latch and the data tag are moveably attached to the lid.

7. The surgical handpiece of claim 1, wherein the latch and the data tag are rotatably mounted to one of the shell or the lid.

8. The surgical handpiece of claim 1, wherein the lid is hingedly attached to the shell.

9. The surgical handpiece of claim 1, wherein the data tag includes at least one magnet.

10. The surgical handpiece of claim 1, wherein the data tag is visually discernible.

11. A surgical handpiece, the surgical handpiece including:
    a shell shaped to define a compartment for receiving a power module, the power module being insertable into and removable from the compartment;
    an energy applicator attached to the shell, the energy applicator configured to when actuated output energy for application to a tissue to perform a medical/surgical task;

a transmission component disposed in the shell for transmitting energy output by the power module to the energy applicator;

a lid moveably mountable to the shell to cover the shell opening;

a latch moveably attached to one of the shell or the lid for holding the lid in a latched state; and a magnet mounted to the latch so as to move with the latch, the magnet being configured to generate a magnetic field, the absence or presence of the magnetic field being determined by a sensor of the power module.

12. The surgical handpiece of claim 11, wherein the presence of the magnetic field indicates that the lid is in the latched state in which the power module is disposed within the compartment.

13. The surgical handpiece of claim 11, wherein the magnet is further defined as a first magnet, the magnetic field is further defined as a first magnetic field, the sensor is further defined as a first sensor, the surgical handpiece further comprising a second magnet mounted to the latch so as to move with the latch, the second magnet being configured to generate a second magnetic field, the presence of the second magnetic field being determined by a second sensor of the power module, the presence of at least one of the first magnetic field and the second magnetic field provides an indication of a type of surgical handpiece.

* * * * *